United States Patent [19]
Gold et al.

[11] Patent Number: 6,124,449
[45] Date of Patent: Sep. 26, 2000

[54] HIGH AFFINITY TGFβ NUCLEIC ACID LIGANDS AND INHIBITORS

[75] Inventors: Larry Gold; Nikos Pagratis, both of Boulder, Colo.

[73] Assignee: NeXstar Pharmaceuticals, Inc., Boulder, Colo.

[21] Appl. No.: 09/046,247

[22] Filed: Mar. 23, 1998

Related U.S. Application Data

[63] Continuation-in-part of application No. 08/458,424, Jun. 2, 1995, Pat. No. 5,731,424, which is a continuation-in-part of application No. 07/931,473, Aug. 17, 1992, Pat. No. 5,270,163, application No. 07/964,624, Oct. 21, 1992, Pat. No. 5,496,938, application No. 08/117,991, Sep. 8, 1993, abandoned, and application No. 07/714,131, Jun. 10, 1991, Pat. No. 5,475,096, which is a continuation-in-part of application No. 07/536,428, Jun. 11, 1990, abandoned.

[51] Int. Cl.[7] .................................................. C07H 21/04
[52] U.S. Cl. ........................... 536/24.3; 435/6; 435/91.2; 536/23.1; 536/25.4
[58] Field of Search ...................... 435/6, 91.2; 536/24.3, 536/23.1, 25.4; 935/77.78

[56] References Cited

U.S. PATENT DOCUMENTS

| | | | |
|---|---|---|---|
| 5,270,163 | 12/1993 | Gold et al. | 435/6 |
| 5,459,015 | 10/1995 | Janjic et al. | 435/6 |

FOREIGN PATENT DOCUMENTS

| | | |
|---|---|---|
| 2 183 661 | 6/1987 | United Kingdom . |
| WO89/06694 | 7/1989 | WIPO . |
| WO92/14843 | 9/1992 | WIPO . |

OTHER PUBLICATIONS

Arteaga et al. (1993) J. Clin. Invest. 92:2569.
Arteaga et al. (1990) Cell Growth & Differentiation 1:367.
Barral et al. (1993) Proc. Natl. Acad. Sci. USA 90:3442.
Ellington and Szostak (1990) Abstract of papers presented at the 1990 meeting on RNA Processing, Cold Spring Harbor Laboratory, Cold Spring Harbor, NY, p. 84.
Joyce (1989) Gene 82:83.
Joyce and Inoue (1989) Nucleic Acids Research 17:711.
Kinzler and Vogelstein (1989) Nucleic Acids Research 17:3645.
Kramer et al. (1974) J. Mol. Biol. 89:719.
Levisohn and Spiegelman (1968) Proc. Natl. Acad. Sci. USA 60:866.
Levisohn and Spiegelman (1969) Proc. Natl. Acad. Sci. USA 63:805.
Oliphant et al. (1986) Gene 44:177.
Oliphant and Struhl (1987) Methods in Enzymology 155:568.
Oliphand and Struhl (1988) Nucleic Acids Research 16:7673.
Oliphant et al. (1989) Mol. Cell. Biol. 9:2944.
Robertson and Joyce (1990) Nature 344:467.
Shah et al. (1992) Lancet 339:213.
Thiesen and Bach (1990) Nucleic Acids Research 18:3203.

*Primary Examiner*—Stephanie W. Zitomer
*Attorney, Agent, or Firm*—Swanson & Bratschun LLC

[57] ABSTRACT

Methods are described for the identification and preparation of high-affinity nucleic acid ligands to TGFβ. Included in the invention are specific RNA ligands to TGFβ1 identified by the SELEX method. Also included are RNA ligands that inhibit the interaction of TGFβ1 with its receptor.

1 Claim, 10 Drawing Sheets

HIGH AFFINITY TGFβ NUCLEIC ACID LIGANDS AND INHIBITORS

RELATED APPLICATIONS

This application is a continuation-in-part of U.S. patent application Ser. No. 08/458,424, filed Jun. 2, 1995, entitled "High Affinity TGFβ Nucleic Acid Ligands and Inhibitors," now issued as U.S. Pat. No. 5,731,424, which is a continuation-in-part of U.S. patent application Ser. No. 07/714,131, filed Jun. 10, 1991, entitled "Nucleic Acid Ligands," now issued as U.S. Pat. No. 5,475,096, U.S. patent application Ser. No. 07/931,473, filed Aug. 17, 1992, entitled "Methods for Identifying Nucleic Acid Ligands," now issued as U.S. Pat. No. 5,270,163, U.S. patent application Ser. No. 07/964,624, filed Oct. 21, 1992, entitled "Nucleic Acid Ligands to HIV-RT and HIV-1 Rev," now issued as U.S. Pat. No. 5,496,938, and U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now issued as U.S. Pat. No. 5,660,985. U.S. Pat. application Ser. No. 07/714,131 is a continuation-in-part of U.S. Pat. application Ser. No. 07/536,428, filed Jun. 11, 1990, entitled "Systematic Evolution of Ligands by EXponential Enrichment," now abandoned.

FIELD OF THE INVENTION

Described herein are methods for identifying and preparing high-affinity nucleic acid ligands to TGFβ. The method utilized herein for identifying such nucleic acid ligands is called SELEX, an acronym for Systematic Evolution of Ligands by EXponential enrichment. This invention includes high affinity nucleic acid ligands of TGFβ. Further disclosed are RNA ligands to TGFβ1. Also included are oligonucleotides containing nucleotide derivatives chemically modified at the 2'-positions of pyrimidines. Additionally disclosed are RNA ligands to TGFβ1 containing 2'-F-modifications. This invention also includes high affinity nucleic acid inhibitors of TGFβ1. The oligonucleotides of the present invention are useful as pharmaceuticals or diagnostic agents.

BACKGROUND OF THE INVENTION

The transforming growth factor-β (TGFβ) polypeptides influence growth, differentiation, and gene expression in many cell types. The first polypeptide of this family that was characterized, TGFβ1 has two identical 112 amino acid subunits which are covalently linked. TGFβ1 is a highly conserved protein with only a single amino acid difference distinguishing humans from mice. There are two other members of the TGFβ gene family that are expressed in mammals. TGFβ2 is 71% homologous to TGFβ1 (de Martin et al. (1987) EMBO J. 6:3673–3677), whereas TGFβ3 is 80% homologous to TGFβ1 (Derynck et al. (1988) EMBO J 7:3737–3743). The structural characteristics of TGFβ1 as determined by nuclear magnetic resonance (Archer et al. (1993) Biochemistry 32:1164–1171) agree with the crystal structure of TGFβ2 (Daopin et al. (1992) Science 257:369–374; Schlunegger and Grutter (1992) Nature 358:430–434) Even though the TGFβ's have similar three dimensional structures, they are by no means physiologically equivalent. There are at least three different extracellular receptors, type I, II and III, involved in transmembrane signaling of TGFβ to cells carrying the receptors. (For reviews, see Derynck (1994) TIBS 19:548–553 and Massague (1990) Ann. Rev. Cell Biol. 6:597–641). In order for TGFβ2 to effectively interact with the type II TGFβ receptor, the type III receptor must also be present (Derynck (1994) TIBS 19:548–553). Vascular endothelial cells lack the type III receptor. Instead endothelial cells express a structurally related protein called endoglin (Cheifetz et al. (1992) J. Biol. Chem. 267:19027–19030), which only binds TGFβ1 and TGFβ3 with high affinity. Thus, the relative potency of the TGFβ's reflect the type of receptor expressed in a cell and organ system.

In addition to the regulation of the components in the multifactorial signaling pathway, the distribution of the synthesis of TGFβ polypeptides also affects physiological function. The distribution of TGFβ2 and TGFβ3 is more limited (Derynck et al. (1988) EMBO J 7:3737–3743) than TGFβ1, e.g., TGFβ3 is limited to tissues of mesenchymal origin, whereas TGFβ1 is present in both tissues of mesenchymal and epithelial origin.

TGFβ1 is a multifunctional cytokine critical for tissue repair. High concentrations of TGFβ1 are delivered to the site of injury by platelet granules (Assoian and Sporn (1986) J. Cell Biol. 102:1217–1223). TGFβ1 initiates a series of events that promote healing including chemotaxis of cells such as leukocytes, monocytes and fibroblasts, and regulation of growth factors and cytokines involved in angiogenesis, cell division associated with tissue repair and inflammatory responses. TGFβ1 also stimulates the synthesis of extracellular matrix components (Roberts et al. (1986) Proc. Natl. Acad. Sci. USA 83:4167–4171; Sporn et al. (1983) Science 219:1329–1330; Massague (1987) Cell 49:437–438) and most importantly for understanding the pathophysiology of TGFβ1, TGFβ1 autoregulates its own synthesis (Kim et al. (1989) J. Biol. Chem. 264:7041–7045).

A number of diseases have been associated with TGFβ1 overproduction. Fibrotic diseases associated with TGFβ1 overproduction can be divided into chronic conditions such as fibrosis of the kidney, lung and liver and more acute conditions such as dermal scarring and restenosis. Synthesis and secretion of TGFβ1 by tumor cells can also lead to immune suppression such as seen in patients with aggressive brain or breast tumors (Arteaga et al. (1993) J. Clin. Invest. 92:2569–2576). The course of Leishmanial infection in mice is drastically altered by TGFβ1 (Barral-Netto et al. (1992) Science 257:545–547). TGFβ1 exacerbated the disease, whereas TGFβ1 antibodies halted the progression of the disease in genetically susceptible mice. Genetically resistant mice became susceptible to Leishmanial infection upon administration of TGFβ1.

The profound effects of TGFβ1 on extracellular matrix deposition have been reviewed (Rocco and Ziyadeh (1991) in *Contemporary Issues in Nephrology* v.23, Hormones, autocoids and the kidney. ed. Jay Stein, Churchill Livingston, New York pp.391–410; Roberts et al. (1988) Rec. Prog. Hormone Res. 44:157–197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGFβ1 has profound effects on the kidney. The accumulation of mesangial matrix in proliferative glomerulonephritis (Border et al. (1990) Kidney Int. 37:689–695) and diabetic nephropathy (Mauer et al. (1984) J. Clin. Invest. 74:1143–1155) are clear and dominant pathological features of the diseases. TGFβ1 levels are elevated in human diabetic glomerulosclerosis (advanced neuropathy) (Yamamoto et al. (1993) Proc. Natl. Acad. Sci. 90:1814–1818). TGFβ1 is an important mediator in the genesis of renal fibrosis in a number of animal models (Phan et al. (1990) Kidney Int. 37:426; Okuda et al. (1990) J. Clin. Invest. 86:453). Suppression of experimentally induced glomerulonephritis in rats has been demonstrated by antiserum against TGFβ1 (Border et al. (1990) Nature 346:371) and by an extracellular matrix protein, decorin, which can bind TGFβ1 (Border et al. (1992) Nature 360:361–363).

Too much TGFβ1 leads to dermal scar-tissue formation. Neutralizing TGFβ1 antibodies injected into the margins of healing wounds in rats have been shown to inhibit scarring without interfering with the rate of wound healing or the tensile strength of the wound (Shah et al. (1992) Lancet 339:213–214). At the same time there was reduced angiogenesis, reduced number of macrophages and monocytes in the wound, and a reduced amount of disorganized collagen fiber deposition in the scar tissue.

TGFβ1 may be a factor in the progressive thickening of the arterial wall which results from the proliferation of smooth muscle cells and deposition of extracellular matrix in the artery after balloon angioplasty. The diameter of the restenosed artery may be reduced 90% by this thickening, and since most of the reduction in diameter is due to extracellular matrix rather than smooth muscle cell bodies, it may be possible to open these vessels to 50% simply by reducing extensive extracellular matrix deposition. In uninjured pig arteries transfected in vivo with a TGFβ1 gene, TGFβ1 gene expression was associated with both extracellular matrix synthesis and hyperplasia (Nabel et al. (1993) Proc. Natl. Acad. Sci. USA 90:10759–10763). The TGFβ1 induced hyperplasia was not as extensive as that induced with PDGF-BB, but the extracellular matrix was more extensive with TGFβ1 transfectants. No extracellular matrix deposition was associated with FGF-1 (a secreted form of FGF) induced hyperplasia in this gene transfer pig model (Nabel (1993) Nature 362:844–846).

There are several types of cancer where TGFβ1 produced by the tumor may be deleterious. MATLyLu rat cancer cells (Steiner and Barrack (1992) Mol. Endocrinol. 6:15–25) and MCF-7 human breast cancer cells (Arteaga et al. (1993) Cell Growth and Differ. 4:193–201) became more tumorigenic and metastatic after transfection with a vector expressing the mouse TGFβ1. In breast cancer, poor prognosis is associated with elevated TGFβ (Dickson et al. (1987) Proc. Natl. Acad. Sci. USA 84:837–841; Kasid et al. (1987) Cancer Res. 47:5733–5738; Daly et al. (1990) J. Cell Biochem. 43:199–211; Barrett-Lee et al. (1990) Br. J Cancer 61:612–617; King et al. (1989) J. Steroid Biochem. 34:133–138; Welch et al. (1990) Proc. Natl. Acad. Sci. USA 87:7678–7682; Walker et al. (1992) Eur. J. Cancer 238:641–644) and induction of TGFβ1 by tamoxifen treatment (Butta et al. (1992) Cancer Res. 52:4261–4264) has been associated with failure of tamoxifen treatment for breast cancer (Thompson et al. (1991) Br. J Cancer 63:609–614). Anti TGFβ1 antibodies inhibit the growth of MDA-231 human breast cancer cells in athymic mice (Arteaga et al. (1993) J. Clin. Invest. 92:2569–2576), a treatment which is correlated with an increase in spleen natural killer cell activity. CHO cells transfected with latent TGFβ1 also showed decreased NK activity and increased tumor growth in nude mice (Wallick et al. (1990) J. Exp. Med. 172:1777–1784). Thus, TGFβ1 secreted by breast tumors may cause an endocrine immune suppression.

High plasma concentrations of TGFβ1 have been shown to indicate poor prognosis for advanced breast cancer patients (Anscher et al. (1993) N. Engl. J. Med. 328:1592–1598). Patients with high circulating TGFβ before high dose chemotherapy and autologous bone marrow transplantation are at high risk for hepatic veno-occlusive disease (15–50% of all patients with a mortality rate up to 50%) and idiopathic interstitial pneumonitis (40–60% of all patients). The implication of these findings is 1) that elevated plasma levels of TGFβ1 can be used to identify at risk patients and 2) that reduction of TGFβ1 could decrease the morbidity and mortality of these common treatments for breast cancer patients.

A method for the in vitro evolution of nucleic acid molecules with high affinity binding to target molecules has been developed. This method, Systematic Evolution of Ligands by EXponential enrichment, termed SELEX, is described in U.S. Pat. application Ser. No. 07/536,428, filed Jun. 11, 1990, entitled "Systematic Evolution of Ligands by Exponential Enrichment," now abandoned, U.S. patent application Ser. No. 07/714,131, filed Jun. 10, 1991, entitled "Nucleic Acid Ligands," now issued as U.S. Pat. No. 5,475,096, U.S. patent application Ser. No. 07/931,473, filed Aug. 17, 1992, entitled "Methods for Identifying Nucleic Acid Ligands," now U.S. Pat. No. 5,270,163 (see also WO91/19813), each of which is herein specifically incorporated by reference. Each of these applications, collectively referred to herein as the SELEX Patent Applications, describe a fundamentally novel method for making a nucleic acid ligand to any desired target molecule.

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled "Method for Selecting Nucleic Acids on the Basis of Structure," now abandoned, describes the use of SELEX in conjunction with gel electrophoresis to select nucleic acid molecules with specific structural characteristics, such as bent DNA. (See U.S. Pat. No. 5,707,796). U.S. patent application Ser. No. 08/123,935, filed Sep. 17, 1993, entitled "Photoselection of Nucleic Acid Ligands," now abandoned, describes a SELEX based method for selecting nucleic acid ligands containing photoreactive groups capable of binding and/or photo-crosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443, 957, now U.S. Pat. No. 5,580,737,describes a method for identifying highly specific nucleic acid ligands able to discriminate between closely related molecules, termed "Counter-SELEX." U.S. patent application Ser. No. 08/143, 564, filed Oct. 25, 1993, entitled "Systematic Evolution of Ligands by EXponential Enrichment: Solution SELEX," abandoned in favor of U.S. patent application Ser. No. 08/461,061, now U.S. Pat. No. 5,567,588) and U.S. patent application Ser. No. 08/792,075, filed Jan. 31, 1997, entitled "Flow Cell SELEX," describe SELEX-based methods which achieve highly efficient partitioning between oligonucleotides having high and low affinity for a Target molecule. U.S. patent application Ser. No. 07/964,624, filed Oct. 21, 1992, entitled "Nucleic Acid Ligands to HIV-RT and HIV-1 Rev," now U.S. Pat. No. 5,496,938, describes methods for obtaining improved Nucleic Acid Ligands after the SELEX process has been performed. U.S. patent application Ser. No. 08/400,440, filed Mar. 8, 1995, entitled "Systematic Evolution of Ligands by EXponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines, as well as specific RNA ligands to thrombin containing 2'-amino modifications. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines. International patent application PCT/US98/00589, filed Jan. 7, 1998, entitled "Bioconjugation of Oligonucleotides," describes a method for identifying bioconjugates to a target comprising nucleic acid ligands derivatized with a molecular entity exclusively at the 5'-position of the nucleic acid ligands.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459 and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties of oligonucleotides with the desirable properties of other molecules. The full text of the above described patent applications, including but not limited to, all definitions and descriptions of the SELEX process, are specifically incorporated herein by reference in their entirety.

BRIEF SUMMARY OF THE INVENTION

The present invention includes methods of identifying and producing nucleic acid ligands to transforming growth factor beta (TGFβ) and the nucleic acid ligands so identified and produced. For the purpose of this application, TGFβ includes human TGFβ1, TGFβ2, TGFβ3 and TGFβ's that are substantially homologous thereto. By substantially homologous it is meant a degree of amino acid sequence identity of 70% or more. In particular, RNA sequences are provided that are capable of binding specifically to TGFβ1. Specifically included in the invention are the RNA ligand sequences shown in Table 3 (SEQ ID NOS:6–143). Also included in this invention are RNA ligands of TGFβ1 that inhibit the function of TGFβ1.

Further included in this invention is a method of identifying nucleic acid ligands and nucleic acid ligand sequences to TGFβ comprising the steps of (a) preparing a candidate mixture of nucleic acids, (b) contacting the candidate mixture of nucleic acids with TGFβ, (c) partitioning between members of said candidate mixture on the basis of affinity to TGFβ, and (d) amplifying the selected molecules to yield a mixture of nucleic acids enriched for nucleic acid sequences with a relatively higher affinity for binding to TGFβ.

More specifically, the present invention includes the RNA ligands to TGFβ identified according to the above-described method, including those ligands shown in Table 3 (SEQ ID NOS:6–143). Also included are nucleic acid ligands to TGFβ that are substantially homologous to any of the given ligands and that have substantially the same ability to bind TGFβ and inhibit the function of TGFβ. Further included in this invention are nucleic acid ligands to TGFβ that have substantially the same structural form as the ligands presented herein and that have substantially the same ability to bind TGFβ and inhibit the function of TGFβ.

The present invention also includes other modified nucleotide sequences based on the nucleic acid ligands identified herein and mixtures of the same.

BRIEF DESCRIPTION OF THE FIGURES

FIGS. 4A and 4B show the inhibitory activity of rounds 11 (■) and 14 (●) of the 40N pool (FIG. 4A) and rounds 11 (■) and 14 (●) of the 30N pool (FIG. 4B) compared to random RNA (▲). The results are expressed as $^3$H-thymidine incorporation as net % of control vs. concentration of TGFβ1, where control is the amount of $^3$H-thymidine incorporation in the absence of TGFβ1 and RNA minus the amount of incorporation in the presence of TGFβ1 alone.

FIG. 5A is a TGFβ1 titration curve presented as $^3$H-thymidine incorporation as a per cent of control vs. concentration of TGFβ1. FIGS. 5B–5D illustrate the bioactivities of round 16 of the 40N pool (FIG. 5B, (●)), ligand 40-03 (FIG. 5C, (●)) and ligand 40-60 (FIG. 5D, (●)) as compared to the bioactivities of a polyclonal anti-TGFβ1 antibody (○) and random RNA (■), presented as $^3$H-thymidine incorporation as a per cent of control vs. concentration of TGFβ1.

DETAILED DESCRIPTION OF THE INVENTION

Figure 1A:
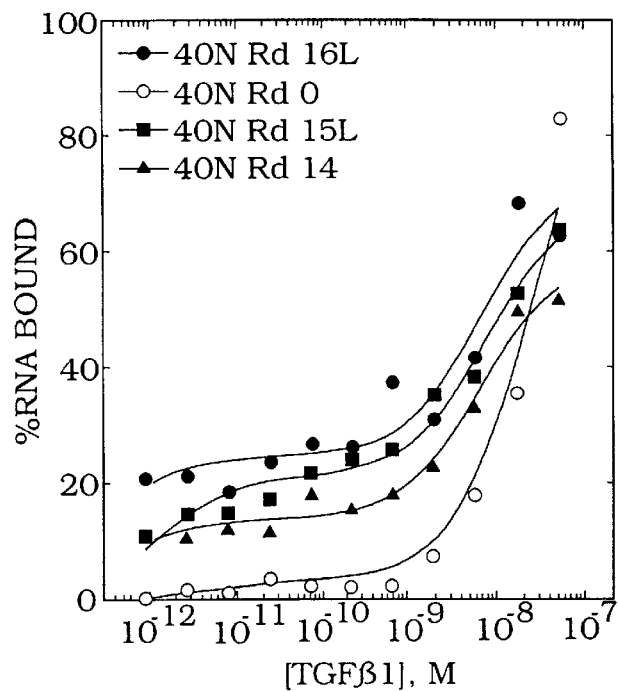
FIGS. 1A and 1B show the binding curves of rounds 0 (○), 14 (▲), 15 (■) and 16 (●) of the 40N pool (FIG. 1A) and rounds 0 (○), 14 (▲), 15 (■) and 17 (●) of the 30N pool (FIG. 1B) presented as % RNA bound vs. concentration of TGFβ1.

This application describes high-affinity nucleic acid ligands to TGFβ identified through the method known as SELEX. SELEX is described in U.S. Pat. application Ser. No. 07/536,428, entitled "Systematic Evolution of Ligands by EXponential Enrichment," now abandoned, U.S. patent application Ser. No. 07/714,131, filed Jun. 10, 1991, entitled "Nucleic Acid Ligands," now U.S. Patent No. 5,475,096, U.S. patent application Ser. No. 07/931,473, filed Aug. 17, 1992, entitled "Methods for Identifying Nucleic Acid Ligands," now U.S. Pat. No. 5,270,163, (see also WO91/19813). These applications, each specifically incorporated herein by reference, are collectively called the SELEX Patent Applications. Certain terms used to described the invention herein are defined as follows.

"Nucleic Acid Ligand" as used herein is a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, and facilitating the reaction between the target and another molecule. In the preferred embodiment, the desirable action is specific binding to a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

"Candidate Mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to TGFβ. The SELEX methodology is described in the SELEX Patent Applications.

"Target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the target is a TGFβ, preferably TGFβ1.

In its most basic form, the SELEX process may be defined by the following series of steps.

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The SELEX method further encompasses combining selected nucleic acid ligands with lipophilic or non-immunogenic, high molecular weight compounds in a diagnostic or therapeutic complex as described in U.S. patent application Ser. No. 08/434,465, filed May 4, 1995, entitled "Nucleic Acid Ligand Complexes." VEGF nucleic acid ligands that are associated with a lipophilic compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes." VEGF nucleic acid ligands that are associated with a lipophilic compound, such as a glycerol lipid, or a non-immunogenic, high molecular weight compound, such as polyalkylene glycol, are further described in U.S. patent application Ser. No. 08/897,351, filed Jul. 21, 1997, entitled "Vascular Endothelial Growth Factor (VEGF) Nucleic Acid Ligand Complexes." VEGF nucleic acid ligands that are associated with a non-immunogenic, high molecular weight compound or lipophilic compound are also further described in PCT/US97/18944, filed Oct. 17, 1997, entitled "Vascular Endothelial Growth Factor (VEGF) Nucleic Acid Ligand Complexes." Each of the above described patent applications which describe modifications of the basic SELEX procedure are specifically incorporated by reference herein in their entirety.

Certain embodiments of the present invention provide a complex comprising one or more nucleic acid ligands to TGFβ covalently linked with a non-immunogenic, high molecular weight compound or lipophilic compound. A complex as used herein describes the molecular entity formed by the covalent linking of the nucleic acid ligand of TGFβ to a non-immunogenic, high molecular weight compound. A non-immunogenic, high molecular weight compound is a compound between approximately 100 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. In a preferred embodiment of the invention, the non-immunogenic, high molecular weight compound is a polyalkylene glycol. In the most preferred embodiment, the polyalkylene glycol is polyethylene glycol (PEG). More preferably, the PEG has a molecular weight of about 10–80K. Most preferably, the PEG has a molecular weight of about 20–45K. In certain embodiments of the invention, the non-immunogenic, high molecular weight compound can also be a nucleic acid ligand.

Another embodiment of the invention is directed to complexes comprised of a nucleic acid ligand to TGFβ and a lipophilic compound. Lipophilic compounds are compounds that have the propensity to associate with or partition into lipids and/or other materials or phases with low dielectric constants, including structures that are comprised substantially of lipophilic components. Lipophilic compounds include lipids as well as non-lipid containing compounds that have the propensity to associate with lipids (and/or other materials or phases with low dielectric constants). Cholesterol, phospholipid and glycerol lipids, such as dialkylglycerol, diacylglycerol, and glycerol amide lipids are further examples of lipophilic compounds. In a preferred embodiment, the lipophilic compound is a glycerol lipid.

The non-immunogenic, high molecular weight compound or lipophilic compound may be covalently bound to a variety of positions on the nucleic acid ligand to TGFβ, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the nucleic acid ligand to TGFβ. In embodiments where the lipophilic compound is a glycerol lipid, or the non-immunogenic, high molecular weight compound is polyalkylene glycol or polyethylene glycol, preferably the non-immunogenic, high molecular weight compound is bonded to the 5' or 3' hydroxyl of the phosphate group thereof. In the most preferred embodiment, the lipophilic compound or non-immunogenic, high molecular weight compound is bonded to the 5' hydroxyl of the phosphate group of the nucleic acid ligand. Attachment of the non-immunogenic, high molecular weight compound or lipophilic compound to the nucleic acid ligand of TGFβ can be done directly or with the utilization of linkers or spacers.

A linker is a molecular entity that connects two or more molecular entities through covalent bonds or non-covalent interactions, and can allow spatial separation of the molecular entities in a manner that preserves the functional properties of one or more of the molecular entities. A linker can also be referred to as a spacer.

The complex comprising a nucleic acid ligand to TGFβ and a non-immunogenic, high molecular weight compound or lipophilic compound can be further associated with a lipid construct. Lipid constructs are structures containing lipids, phospholipids, or derivatives thereof comprising a variety of different structural arrangements which lipids are known to adopt in aqueous suspension. These structures include, but are not limited to, lipid bilayer vesicles, micelles, liposomes, emulsions, lipid ribbons or sheets, and may be complexed with a variety of drugs and components which are known to be pharmaceutically acceptable. In the preferred embodiment, the lipid construct is a liposome. The preferred liposome is unilamellar and has a relative size less than 200 nm. Common additional components in lipid constructs include cholesterol and alpha-tocopherol, among others. The lipid constructs may be used alone or in any combination which one skilled in the art would appreciate to provide the characteristics desired for a particular application. In addition, the technical aspects of lipid constructs and liposome formation are well known in the art and any of the methods commonly practiced in the field may be used for the present invention.

The SELEX method further comprises identifying bioconjugates to a target. Copending and commonly assigned PCT Patent Application No. PCT/US98/00589, filed Jan. 7, 1998, entitled "Bioconjugation of Oligonucleotides," describes a method for enzymatically synthesizing bioconjugates comprising RNA derivatized exclusively at the 5'-position with a molecular entity, and a method for identifying bioconjugates to a target comprising nucleic acid ligands derivatized with a molecular entity exclusively at the 5'-position of the nucleic acid ligands. A bioconjugate as used herein refers to any oligonucleotide which has been derivatized with another molecular entity. In the preferred embodiment, the molecular entity is a macromolecule. As used herein, a macromolecule refers to a large organic molecule. Examples of macromolecules include, but are not limited to nucleic acids, oligonucleotides, proteins, peptides, carbohydrates, polysaccharides, glycoproteins, lipophilic compounds, such as cholesterol, phospholipids, diacyl glycerols and dialkyl glycerols, hormones, drugs, non-immunogenic high molecular weight compounds, fluorescent, chemiluminescent and bioluminescent marker compounds, antibodies and biotin, etc. without limitation. In certain embodiments, the molecular entity may provide certain desirable characteristics to the nucleic acid ligand, such as increasing RNA hydrophobicity and enhancing binding, membrane partitioning and/or permeability. Additionally, reporter molecules, such as biotin, fluorescein or peptidyl metal chelates for incorporation of diagnostic radionuclides may be added, thus providing a bioconjugate which may be used as a diagnostic agent.

Certain embodiments of the present invention provide bioconjugates to TGFβ comprising RNA derivatized exclusively at the 5'-position with a molecular entity obtained by the enzymatic method described in PCT/US98/00589. Other embodiments of the present invention provide bioconjugates to TGFβ comprising a nucleic acid ligand covalently bonded to a macromolecule, obtained from a candidate mixture of bioconjugates, obtained by the method described in PCT/US98/00589.

The methods described herein and the nucleic acid ligands identified by such methods are useful for both therapeutic and diagnostic purposes. Therapeutic uses include the treatment or prevention of diseases or medical conditions in human patients. Therapeutic uses may also include veterinary applications.

Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art or by the methods described in PCT/US98/00589, supra. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to TGFβ described herein may specifically be used for identification of the TGFβ protein.

SELEX provides high affinity ligands of a target molecule. This represents a singular achievement that is unprecedented in the field of nucleic acids research. The present invention applies the SELEX procedure to the specific target of TGFβ1. In the Example section below, the experimental parameters used to isolate and identify the nucleic acid ligands to TGFβ1 are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In the present invention, SELEX experiments were performed in order to identify RNA ligands with specific high affinity for TGFβ1 from degenerate libraries containing 20, 30 or 40 random positions (20N, 30N or 40N) (Table 1). This invention includes the specific RNA ligands to TGFβ1 shown in Table 3 (SEQ ID NOS:6–143), identified by the methods described in Examples 1 and 2. This invention further includes RNA ligands to TGFβ1 which inhibit TGFβ1 function, presumably by inhibiting the interaction of TGFβ1 with its receptor. The scope of the ligands covered by this invention extends to all nucleic acid ligands of TGFβ, modified and unmodified, identified according to the SELEX procedure. More specifically, this invention includes nucleic acid sequences that are substantially homologous to the ligands shown in Table 3 (SEQ ID NOS:6–143). By substantially homologous it is meant a degree of primary sequence homology in excess of 70%, most preferably in excess of 80%, and even more preferably in excess of 90%, 95% or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. A review of the sequence homologies of the ligands of TGFβ shown in Tables 3 (SEQ ID NOS:6–143) shows that some sequences with little or no primary homology may have substantially the same ability to bind TGFβ. For this reason, this invention also includes nucleic acid ligands that have substantially the same structure and ability to bind TGFβ as the nucleic acid ligands shown in Table 3 (SEQ ID NOS:6–143). Substantially the same ability to bind TGFβ means that the affinity is within one or two orders of magnitude of the affinity of the ligands described herein. It is well within the skill of those of ordinary skill in the art to determine whether a given sequence—substantially homologous to those specifically described herein—has substantially the same ability to bind TGFβ.

This invention also includes nucleic acid ligands that have substantially the same postulated structure or structural motifs. Substantially the same structure or structural motifs can be postulated by sequence alignment using the Zuker-fold program (see Zuker (1 989) Science 244:48–52) as would be known in the art, other computer programs can be used for predicting secondary structure and structural motifs. Substantially the same structure or structural motif of nucleic acid ligands in solution or as a bound structure can also be postulated using NMR or other techniques as would be known in the art.

One potential problem encountered in the therapeutic, prophylactic, and in vivo diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now issued as U.S. Pat. No. 5,660,985 and U.S. patent application Ser. No. 08/434,465, filed May 4, 1995, entitled "Nucleic Acid Ligand Complexes," which are specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil, backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the nucleic acid ligands are derived by the SELEX method, the modifications can be pre- or post-SELEX modifications. Pre-SELEX modifications yield nucleic acid ligands with both specificity for their SELEX Target and improved in vivo stability. Post-SELEX modifications made to 2'-OH nucleic acid ligands can result in improved in vivo stability without adversely affecting the binding capacity of the nucleic acid ligand. The preferred modifications of the nucleic acid ligands of the subject invention are 5' and 3' phosphorothioate capping and/or 3'–3' inverted phosphodiester linkage at the 3' end. In one preferred embodiment, the preferred modification of the nucleic acid ligand is a 3'-3' inverted phosphodiester linkage at the 3' end. Additional 2'-fluoro (2'-F) and/or 2'-amino (2'-NH$_2$) and/or 2'-O methyl (2'-OMe) modification of some or all of the nucleotides is preferred. Described herein are nucleic acid ligands that were 2'-F modified and incorporated into the SELEX process.

Other modifications are known to one of ordinary skill in the art. Such modifications may be made post-SELEX (modification of previously identified unmodified ligands) or by incorporation into the SELEX process.

As described above, because of their ability to selectively bind TGFβ, the nucleic acid ligands to TGFβ described herein are useful as pharmaceuticals. This invention, therefore, also includes a method for treating TGFβ-mediated pathological conditions by administration of a nucleic acid ligand capable of binding to TGFβ.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following Examples are provided to explain and illustrate the present invention and are not intended to be limiting of the invention. Example 1 describes the various materials and experimental procedures used in Example 2. Example 2 describes a representative method for identifying RNA ligands by the SELEX method which bind TGFβ1. Example 3 describes the affinities the ligands have for TGFβ1. Example 4 describes the specificity of ligands to hTGFβ1. Example 5 describes the inhibition of TGFβ1 bioactivity with several ligands. Example 6 summarizes the results of the data from Examples 2–5. Example 7 describes the proposed secondary structure of bioactive TGFβ1 ligands.

EXAMPLES

Example 1

Experimental Procedures a) Materials

Recombinant human Transforming Growth Factor Beta 1 (hTGFβ1) was purchased from R&D Systems (Minneapolis, Minn.). Mink Lung Epithelial Cells (MLEC) were obtained from American Type Culture Collection (MV 1 Lu ATCC No. CCL 64). T7 RNA polymerase, 2'-F-modified CTP and UTP were prepared in house. DNA oligonucleotides were obtained from Operon Technologies, Inc. (Alameda, Calif.). All other reagents and chemicals were from commercial sources.

b) SELEX

The SELEX process has been described in detail in U.S. Pat. No. 5,270,163 (see also Tuerk and Gold (1990) Science 249:505–510). The DNA templates contained either 40 (SEQ ID NO:1), 30 (SEQ ID NO:2) or 20 (SEQ ID NO:3) random nucleotides, flanked by 5' and 3' constant regions for primer annealing sites for PCR and cDNA synthesis (Table 1). The starting pool of single stranded DNA molecules were converted to double stranded DNA by primer extension reactions with the klenow fragment of DNA polymerase. RNA pools were prepared by transcription and were gel purified before use. Transcription reactions were done with about 5 µM DNA template, 5 units/µL T7 RNA polymerase, 40 mM Tris-HCl (pH 8), 12 mM MgCl$_2$, 5 mM DTT, 1 mM spermidine, 0.002% Triton X-100, 4% PEG 8000, 2–4 mM each 2'-OH ATP, 2'-OH GTP, 2'-F CTP, 2'-F UTP, and 0.25 µM α-$^{32}$P-2'-OH ATP (800 Ci/mmole). At later rounds, RNA pools were prefiltered and/or preadsorbed with multiple layers of the same nitrocellulose filter type used in the SELEX process in order to reduce the frequency of molecules selected for nitrocellulose binding. To prepare binding reactions, the RNA molecules were incubated with recombinant hTGFβ1 in Dulbecco's Phosphate-Buffered Saline (DPBS) (Life Technologies, Gaithersburg, Md., Cat. No 21600-010) containing 0.01% human serum albumin and 1.0 mM MgCl$_2$. Following incubation at 37° C. (10 minutes to 10 hours) the protein-RNA complexes were partitioned from unbound RNA by capture on nitrocellulose. Nitrocellulose filter bound RNA was recovered by phenol/urea extraction. The partitioned RNA was reverse transcribed into cDNA by AMV reverse transcriptase at 48° C. for 60 minutes in 50 mM Tris-HCl pH 8.3, 60 mM NaCl, 6 mM Mg(OAc)$_2$, 10 mM DTT, 50 pmol DNA 3' primer 3G7 (SEQ ID NO:5; Table 1), 0.4 mM each of dATP, dCTP, dGTP, and dTTP, and 1 unit/µL AMV RT. The cDNA was PCR amplified and used to initiate the next SELEX cycle. PCR conditions were 2 µM each 3G7 (SEQ ID NO:5) and 5G7 (SEQ ID NO:4) primers (Table 1), 50 mM KCl, 10 mM Tris-HCl, pH 9, 0.1% Triton X-100, 3 mM MgCl$_2$, 0.5 mM of each dATP, dCTP, dGTP, and dTTP, and 0.1 units/µL Taq DNA polymerase.

c) Nitrocellulose Filter Partitioning

To partition the protein-RNA complexes away from uncomplexed RNA, the binding reactions were filtered through nitrocellulose/cellulose acetate mixed matrix, 0.45 µm pore size filter disks, type HA, (Millipore, Co., Bedford, Mass.). For filtration, the filters were placed onto a vacuum manifold and wetted by aspirating with 5 mL of DPBS. The binding reactions were aspirated through the filters, washed with 5 mL of DPBS+MgCl$_2$ and counted in a scintillation counter (Beckmann). At later rounds, nitrocellulose filters were preblocked with 2 mL of DPBS+1 mM MgCl$_2$+0.01% BSA, and wash volumes were increased to 25 mL in order to reduce background binding to nitrocellulose. At later rounds in the SELEX process, 10 mL washes with 0.5 M urea were introduced to remove RNA that binds to nitrocellulose.

Nitrocellulose partitioning was also used for determining the equilibrium dissociation constants of RNA ligands to hTGFβ1. Binding curves obtained by nitrocellulose filtration indicated that RNA pools and some RNA ligands bind monophasically while others bind biphasically. Biphasic binding can be described as the binding of two affinity species derived from the same ligand sequence that can fold into alternate structures which are kinetically trapped and are not in equilibrium.

To obtain the equilibrium dissociation constants of RNA ligands to TGFβ1, the binding reaction:

where R=RNA, P=Protein and K$_D$=dissociation constant is converted into an equation for the fraction of RNA bound at equilibrium:

$$q=(f/2R_T)(P_T+R_T+K_D-((P_T+R_T+K_D)^2-4P_TR_T)^{1/2})$$

where q=fraction of RNA bound, P$_T$=total protein concentration, R$_T$=total RNA concentration and f=retention efficiency of RNA-protein complexes. The average retention efficiency for RNA-hTGFβ1 complexes on nitrocellulose filters is 0.4–0.8.

Biphasic binding data were evaluated using the equation:

$$q=2P_T+R_T+K_{D1}+K_{D2}-[(P_T+X_1R_1+K_{D1})^2-4P_TX_1R_T]^{1/2}-[(P_T+X_2R_T+K_{D2})^2-4P_TX_2R_T]^{1/2}$$

where X$_1$ and X$_2$ are the mole fractions of the affinity species R$_1$ and R$_2$ and K$_{D1}$ and K$_{D2}$ are the corresponding dissociation constants.

The K$_D$'s were determined by least square fitting of the data points using the software Kaleidagraph (Synergy Software, Reading, Pa.).

d) Cloning and Sequencing

RNA recovered from the filters of the final round of the SELEX process was reverse transcribed and PCR amplified as in previous rounds. The PCR products were purified by PAG electrophoresis and cloned into the SrfI restriction site of PCR-Script Direct SK(+) plasmid using the pCR-Script Amp SK(+) cloning kit (STRATAGENE CLONING SYSTEMS, La Jolla, Calif.). About 180 clones were sequenced with ABI Prism sequencing kit (Applied Biosystems, Perkin-Elmer, Conn.).

e) Analysis of Nucleic Acid Ligand Binding by BIACore

Biotinylated TGFβ1 (catalog No. NFTG0, R&D Systems, Minneapolis, Minn.) was coupled onto an SA5 streptavidin BIAcore chip (BIAcore, Inc., Piscataway, N.J.) by injecting biotinylated TGFβ1 solution as prepared per manufacturers instructions at 5 µL/min to achieve loadings of 436, 133 and 57 response units (RU) in flow cells 1, 2 and 3, respectively. Flow cell 4 was kept blank for control and background subtractions. To measure binding activities, RNA ligands and antiserum (pan-specific anti-TGFβ1 total rabbit IgG, catalog No. AB-100-NA, R&D Systems, Minneapolis, Minn.) were injected at various concentrations in HBSMC-HSA (Hepes buffered saline pH 7.5, 1 mM MgCl$_2$, 1 mM CaCl$_2$, 0.01% human serum albumin) at 20 µL/min. Injections allowed about 3 minute association and 3 minute dissociation cycles. Data were plotted and analyzed by Bianalysis software (BIAcore, Inc., Piscataway, N.J.).

f) Analysis of Nucleic Acid Ligand Specificity by BIACore

Biotinylated 2'-fluoro-pyrimidine RNA nucleic acid ligands were transcribed in the presence of 5'-biotin-modified guanosine monophosphate (5'-biotin-GAP) as described in copending PCT Application No. PCT/US98/00589, filed Jan. 7, 1998, the contents of which are incorporated herein by reference. Typical reactions were 1 mL in volume containing standard T7 RNA polymerase, 40 mM Tris-HCl (pH 8), 12 mM MgCl$_2$, 5 mM DTT, 1 mM spermidine, 0.002% Triton X-100, 4% PEG 8000, with 3 mM each 2'-F-CTP and 2'-F-UTP, and 1 mM each ATP and GTP and 5 mM 5'-biotin GAP. Following overnight incubation at 37° C., transcripts were purified by gel electrophoresis and ethanol precipitation.

To prepare an analysis chip, three RNA species were used and were injected in HBSMC-HSA at 5 µL/min. Flow-cells 1, 2 and 3 were loaded with 535, 536 and 563 RU of random 40N7 library, TGFβ1 ligand 40-03 (SEQ ID NO:84), and TGFβ1 ligand 40-60 (SEQ ID NO:128), respectively. Thus, for stoichiometric binding of RNA to TGFβ1 or TGFβ2, one would expect a maximum of approximately 500 RU's, since TGFβ1 and TGFβ2 have the same mass as the RNA. Flow cell 4 was kept blank for control and background subtractions. The analysis chip was exposed to various concentrations of TGFβ1 and TGFβ2 at 20 µL/min. in HBSMC-HSA.

Data were plotted and analyzed by Bianalysis software (BIAcore, Inc., Piscataway, N.J.).

g) Inhibition of TGFβ1 Mediated Growth Suppression of Mink Lung Epithelial Cells (MLEC)

To determine the bioactivity of RNA pools and individual ligands, a growth assay was used in which TGFβ1 antagonists cause reversal of TGFβ1 growth suppression of mink lung epithelial cells. In this assay, MLEC were treated with various concentrations of random RNA, individual ligands, antibodies such as polyclonal anti-TGFβ1 antibody (pan-specific anti-TGFβ1 total rabbit IgG, catalog No. AB-100-NA, R&D Systems, Minneapolis, Minn.), monoclonal mouse anti-TGFβ2/TGFβ3 antibody (Genzyme Corp., Cambridge Mass., catalog No. 1836-01) and monoclonal mouse anti-TGFβ1/TGFβ2/hTGFβ3 antibody (Genzyme Corp., Cambridge, Mass., catalog No. 1835-01) in serum-free 48 hr-3T3-conditioned medium (CM).

Cells were plated at $10^5$/mL in 96-well plates in MEM, 10 mM HEPES and 0.2% FBS. Following 4 hours of incubation at 37° C., when cells appeared to attach to the well surface, TGFβ1 was added at 2 pM with or without TGFβ1 ligands that ranged from 0.1 nM to 1 µM. In a second assay performed in order to determine cross-species reactivity, rather than using hTGFβ, a conditioned serum-free medium (CM) was used. CM was conditioned by culturing it in murine 3T3 fibroblast for 48 hours. Before use, this conditioned medium was heat treated at 80° C. for 10 minutes to activate the 3T3 cell derived TGFβ and then it was diluted to 50% and supplemented with 0.2% murine serum. In each assay, hTGFβ1 (or CM) was diluted appropriately in MEM and FBS (0.2% or murine serum) and the ligands were diluted in MEM. TGFβ1 (or CM) and ligand dilutions at 10× the final concentration were premixed at equal volumes and then were added to the cells. Following addition of the TGFβ1 (or CM)-ligand mixture, the cells were incubated for 16–18 hours prior to addition of $^3$H-thymidine at 0.25 µCi per well and continued incubation for 7–8 additional hours. After incubation, the cells were washed and harvested with SKATRON filtering units and $^3$H-thymidine incorporation in cellular DNA was quantitated by scintillation counting in Ecoscint. Data were plotted and analyzed as described in Park et al. (1990) J. Exp. Med. 171:1073) and Dower et al. (1984) J. Immunol. 132:751). $K_i$ values were determined from inhibition $IC_{50}$ values according to the equation $K_i = IC_{50}/(1+([T]/K_{dT})$, where [T] is the concentration in molar of TGFβ1 present in the assay and $K_{dT}$ is the concentration of TGFβ1 causing 50% inhibition of MLEC proliferation as determined by TGFβ1 titration experiments.

Example 2

RNA ligands to hTGFβ1 a) TGFβ1 SELEX

Figure 1B:
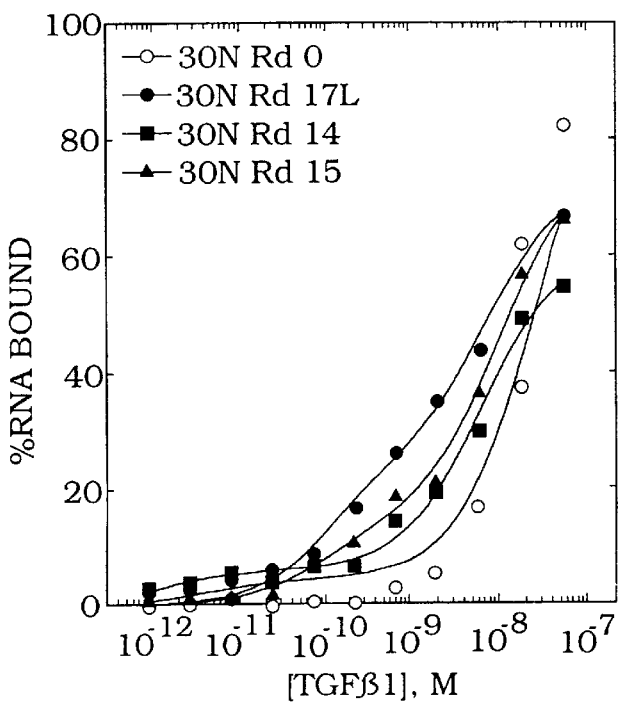

Three parallel SELEX processes were performed with 2'-F pyrimidine modified RNA randomized at 40, 30 and 20 contiguous positions. The conditions for the SELEX process and results for each round are summarized in Table 2. The first round was done under two different conditions where RNA to protein ratios were 10:1 and 50:1. Each condition included a pool of 1.2×10$^{15}$ (2000 pmoles) 2'-F pyrimidine modified RNA molecules. Resulting round 1 pools were mixed (at the transcription level) in equal portions for round 2. Random 2'-F pyrimidine modified RNA bound to hTGFβ1 with an approximate $K_D$ of ~10 nM. The rounds of the SELEX process were continued until no further improvement in $K_D$ was observed. FIGS. 1A and 1B show binding curves of rounds 0, 14, 15L and 16L of the 40N pool (FIG. 1A) and rounds 0, 14, 15 and 17 of the 30N pool (FIG. 1B). The 40N pools showed the best affinity improvement followed by the 30N pool. The 20N pool showed no significant improvement after 12 rounds of SELEX. The RNA pools from the final rounds (round 16, 17 and 12 for the 40N, 30N and 20N, respectively) were reverse transcribed, PCR amplified and cloned as previously described (Pagratis et al. (1997) Nature Biotechnology 15:68–73). The 20N pool was cloned and sequenced as a control.

b) RNA Sequences

The sequences of 64, 48, and 40 clones from the 40N, 30N and 20N final evolved pools, respectively, were determined and are summarized in Table 3 (SEQ ID NOS:6–143) in standard single letter code (Cornish-Bowden (1985) Nucleic Acid Res. 13:3021–3030). Ligand designations in Table 3 include the size of the contributing random region followed by the ligand ID number. Ligands appearing more than once are designated with multiple ID numbers corresponding to their frequency. Ligands differing by one base are considered PCR derived variants of the same original molecule. Computer assisted global and local alignments suggest alignments and family assignments as shown in Table 4. There are 9 proposed families of which the first three include only 40N ligands. The remaining families contain clones derived from all three pools. However, it is clear from sequence lengths that cross contamination of the three pools had occurred. The possibility of cross contamination was minimized by electrophoretic size fractionation of RNA at each round, and PCR products prior to cloning.

Example 3

Binding Affinities of HTGFβ1 Ligands

Figure 2:
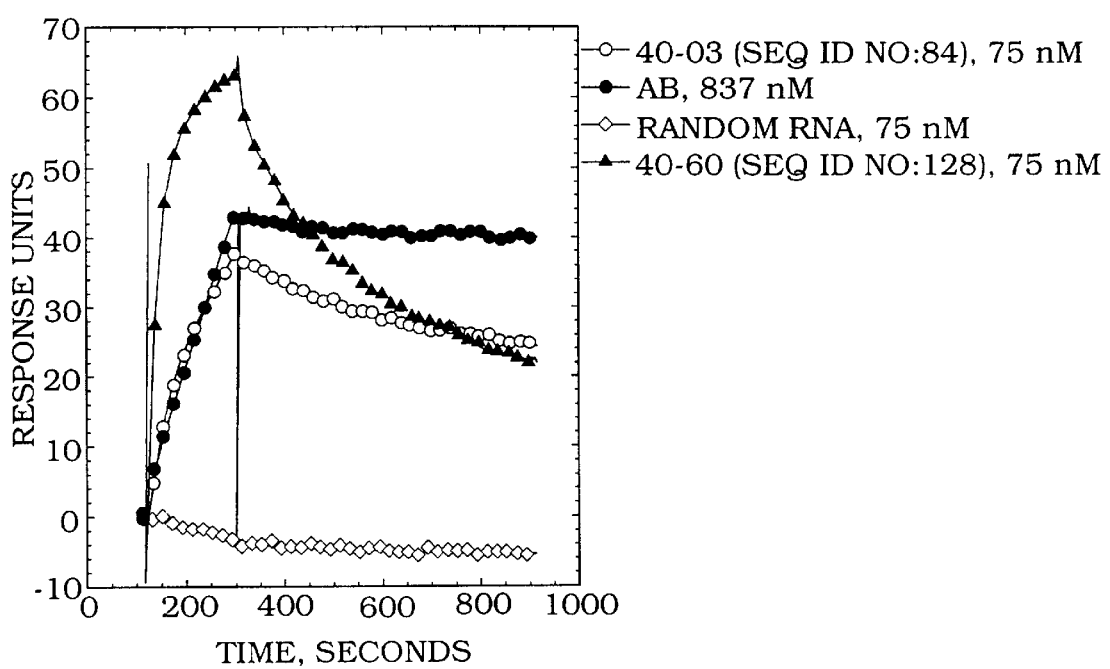
FIG. 2 shows the affinity sensorgram of random RNA (◇), ligand 40-03 (○), ligand 40-60 (▲) and polyclonal anti TGFβ1 antibody (●) performed on TGFβ1, expressed as response units vs. time.

The dissociation constants of the hTGFβ1 ligands were determined by nitrocellulose filter binding and are listed in Table 4. The majority of ligands bind hTGFβ1 biphasically. Under conditions of protein excess, biphasic binding suggests that ligands can exist as two affinity species (presumably isoconformers) that are not in equilibrium, i.e. isoconformers that are kinetically trapped. The best identified ligands, 40-03 (SEQ ID NO:84) and 40-60 (SEQ ID NO:128) bind biphasically with the high and low affinity dissociation constant of ligand 40-03 at about 0.3 pM and 4.6 nM, respectively. There are observed variabilities in the $K_D$ determinations for individual clones and random RNA, however, the high affinity species of ligands 40-03 and 40-60 always show about >10$^4$ better affinity than random RNA in any given experiment. A significant difference between random RNA and ligands 40-03 and 40-60 was also observed by BIAcore analysis. In the BIAcore analysis, biotinylated TGFβ1 was coupled to a BIAcore chip and exposed to various concentrations of random RNA, ligand 40-03 and ligand 40-60. Also in this experiment the binding activities of ligands 40-03 and 40-60 were compared with the binding activity of an anti-TGFβ1 polyclonal antibody (catalog No. AB-100-NA, R&D Systems, Minneapolis, Minn.). FIG. 2 shows the ligand binding of the random RNA, ligands 40-03 and 40-60, and of the anti-TGFβ1 antibody. From these Biacore data the determined dissociation rate constant (k off) for ligand 40-03, ligand 40-60 and anti-TGFβ1 were about 2.7×10$^{-4}$, 7.0×10$^{-4}$ and 4.4×10$^{-5}$, Therefore, ligands 40-03 and 40-60 show binding properties similar to the control antibody with the off rate of 40-03 being about 6 fold faster than the off rate of the anti-TGFβ1.

Example 4

Specificity of RNA Ligands to hTGFβ1

The specificity of ligands 40-03 (SEQ ID NO:84) and 40-60 (SEQ ID NO:128) to TGFβ1 was tested by comparing their dissociation constants with the closely related protein TGFβ2 and the heparin binding human growth factors hVEGF and hKGF. The results summarized in Table 5 show that ligands 40-03 and 40-60 are specific for hTGFβ1. Ligands 40-03 and 40-60 have binding affinities similar to random RNA to the other proteins tested. These ligands are four to five orders of magnitude more specific for TGFβ1 than even closely related proteins such as TGFβ2 and other heparin binding growth factors. Of particular interest is the ability of these TGFβ1 ligands to discriminate between TGFβ1 and TGFβ2 since these two proteins share 72% identity and are interchangeable in most biological assays (Roberts and Sporn (1991), "The Transforming Growth Factor-B's" in *Peptide Growth Factors and Their Receptors*, M. B. Sporn and A. B. Roberts, eds. (New York: Springer-Verlag)). Recently the solution three-dimensional structure of TGFβ1 has been described and compared to the X-ray structure of TGFβ2 (Hinck et al. (1996) Biochemistry 35:8517–8534). Based on this comparison there is only a slight structural difference between TGFβ1 and TGFβ2 with a maximum root mean square deviation of 1.9 Å (Hinck et al. (1996) Biochemistry 35:8517–8534). BIAcore technology was also utilized to compare the binding specificity of ligands 40-03 and 40-60 between TGFβ1 and TGFβ2. The analysis chip, loaded with either biotinylated 40-03, biotinylated 40-60, or biotinylated random RNA was exposed to various concentrations of TGFβ1 or TGFβ2 at 20 μL/min in HBSMC-HSA, and data was collected during the association phase (3 min) and the dissociation phase (3 min).

Figure 3A:
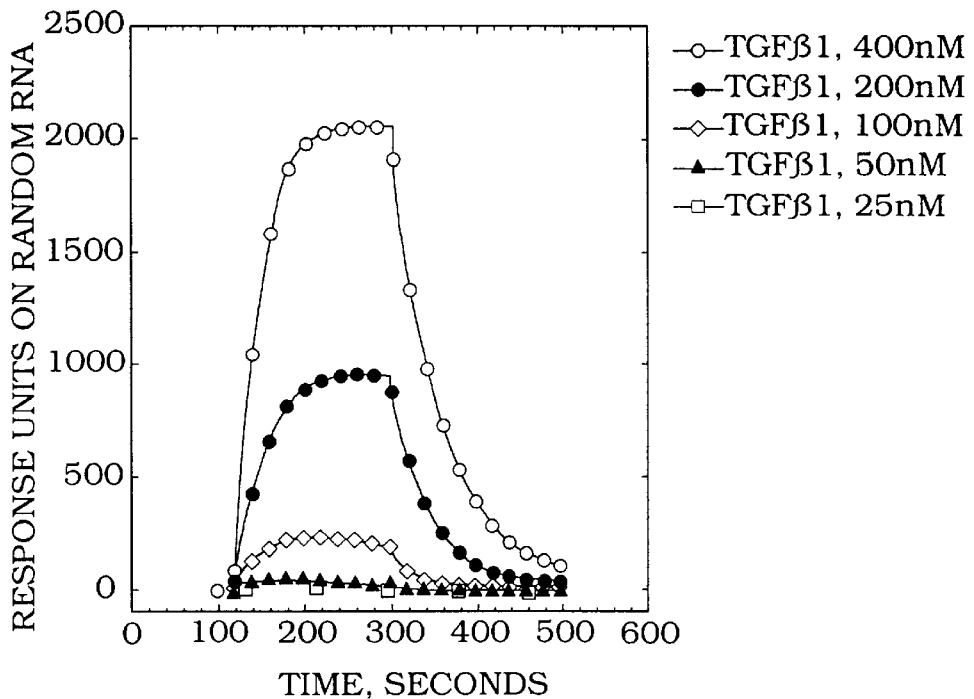
FIGS. 3A–3C show sensorgrams obtained in a binding specificity analysis of TGFβ1 performed on random RNA (FIG. 3A), ligand 40-03 (FIG. 3B) and ligand 40-60 (FIG. 3C) with various concentrations of TGFβ1, expressed as response units vs. time.
Figure 3B:
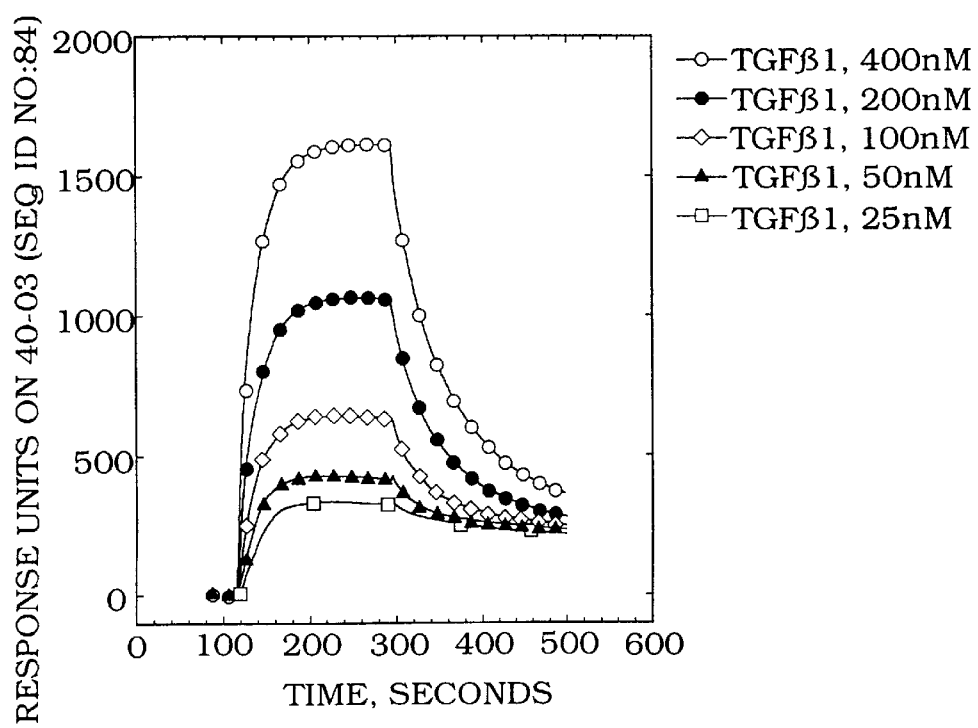
Figure 3C:
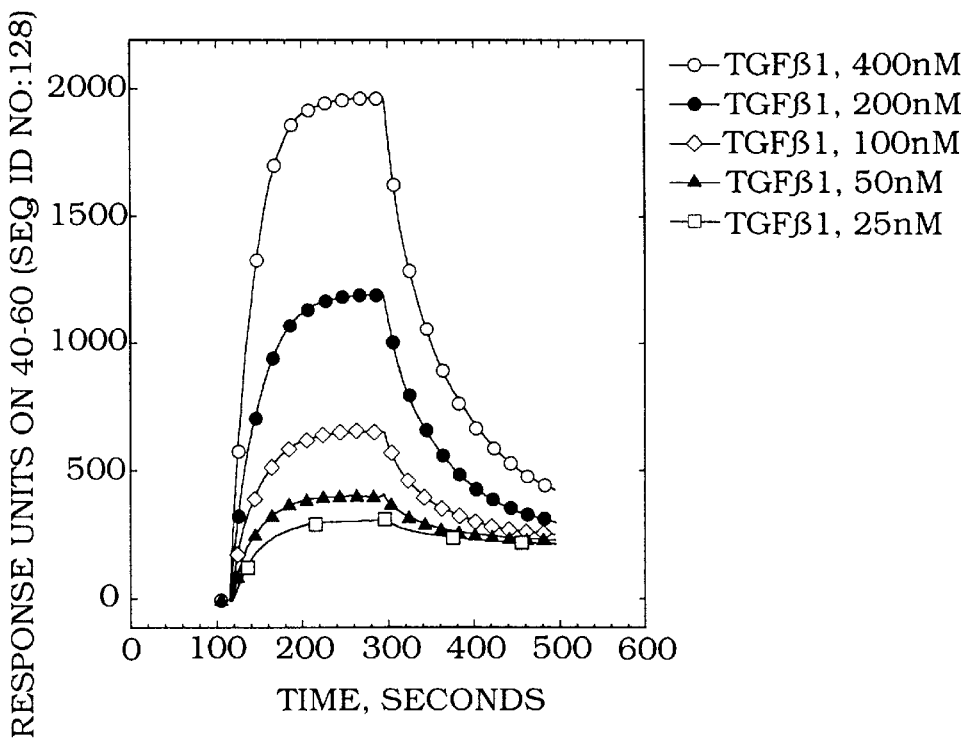
Figure 3D:
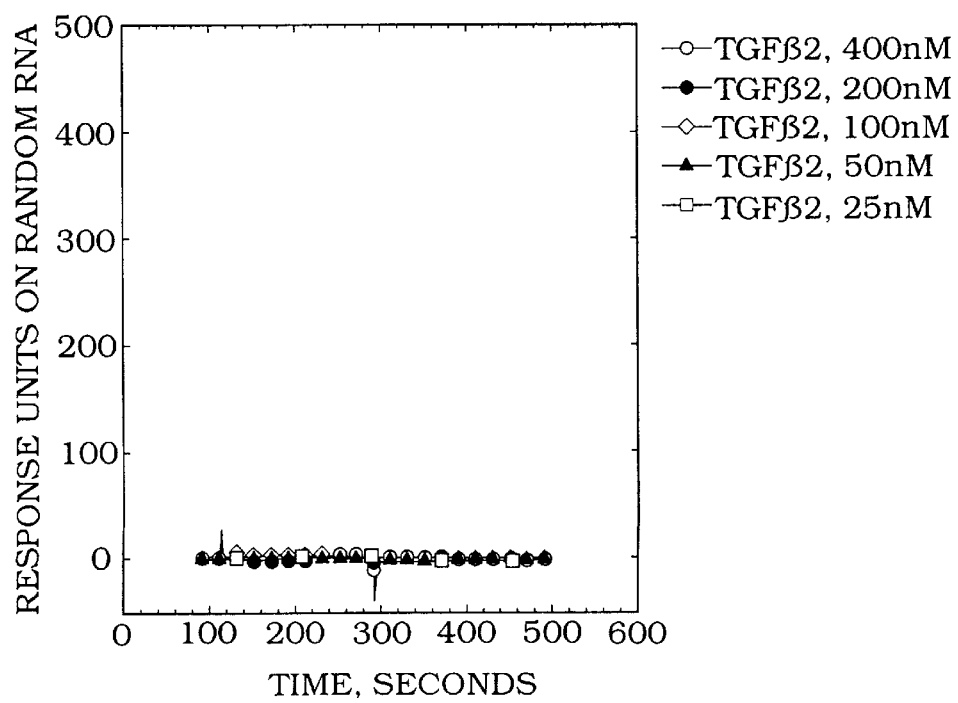
FIGS. 3D–3F show sensorgrams obtained in a binding specificity analysis of TGFβ2 performed on random RNA (FIG. 3D), ligand 40-03 (FIG. 3E) and ligand 40-60 (FIG. 3F) with various concentrations of TGFβ2, expressed as response units vs. time.
Figure 3E:
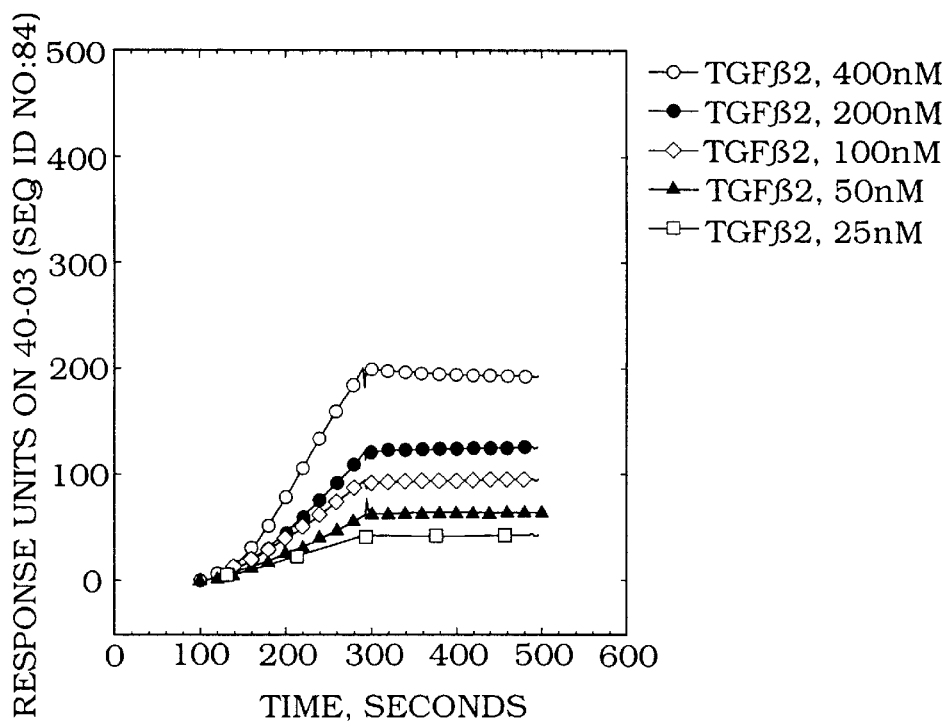
Figure 3F:
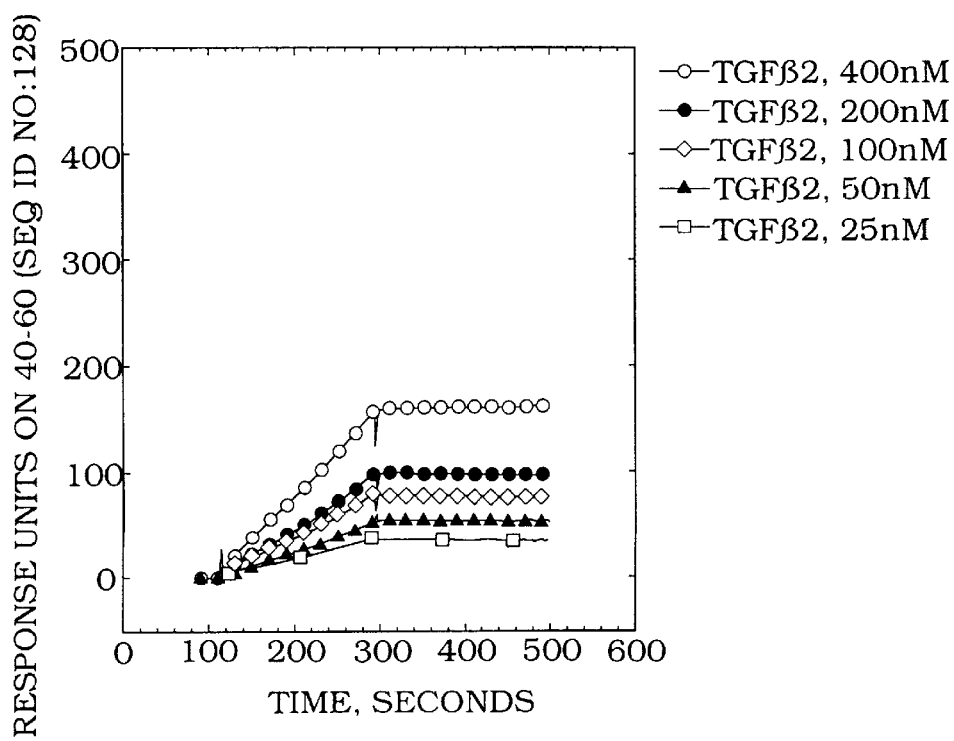

FIGS. 3A–3F show a typical nested series of sensorgrams with TGFβ1 and TGFβ2 binding to random RNA, ligand 40-03 and ligand 40-60. These BIAcore results show that when applied at high concentrations, TGFβ1 binds random RNA (FIG. 3A), ligand 40-03 (FIG. 3B) and ligand 40-60 (FIG. 3C) equivalently in a nonspecific manner with fast on-rates and off-rates. This non-specific binding is low affinity and non-stoichiometric, since stoichiometric binding would result in about 500 RU's of TGFβ1 bound to the RNA on the chip (see Example 1(f)). This non-specific binding represents the binding of random RNA to TGFβ1 also observed by nitrocellulose filter binding (see Example 2(a)). When applied at lower concentrations, (less than 50 nM) TGFβ1 binds ligand 40-03 and 40-60 but not random RNA. The specificity of TGFβ1 for ligands 40-03 and 40-60 is mainly due to slower off rates compared to random RNA. This represents a specific interaction which appears to be stoichiometric, since the binding curves at this concentration plateau at about 400 RU's and the dissociation rates are very slow. See, for example, the triangles in FIG. 3B, in which the dissociation rate is almost flat. TGFβ2 behaves differently in the same experiment. TGFβ2 shows no binding to random RNA (FIG. 3D) and some binding to ligand 40-03 (FIG. 3E) and ligand 40-60 (FIG. 3F). This difference in binding affinity to random RNA is consistent with the increased negative charge content of TGFβ2 compared to TGFβ1. The results in FIGS. 3D–3F clearly show that TGFβ2 binds ligands 40-03 and 40-60 better than random RNA. However, the observed TGFβ2 binding to ligand 40-03 and 40-60 is still different, and lower than the corresponding binding of TGFβ1. It seems that TGFβ2 binds ligand 40-03 and 40-60 with a very slow on and off rate suggesting induced fit. These results suggest that ligands 40-03 and 40-60 show cross-reactivity and bind to both TGFβ1 and TGFβ2 but with different affinities and kinetics.

Example 5

Inhibition of TGFβ1 bioactivity

TGFβ1 is a multifunctional growth factor (Roberts and Sporn, supra). One of its activities is inhibition of proliferation of epithelial cells. For example, TGFβ1 causes mink lung epithelial cells (MLEC) to cease replication, and it is manifested by reduction in $^3$H-thymidine incorporation. The midpoint of this response of MLEC is about 0.3 pM.

Figure 4A:
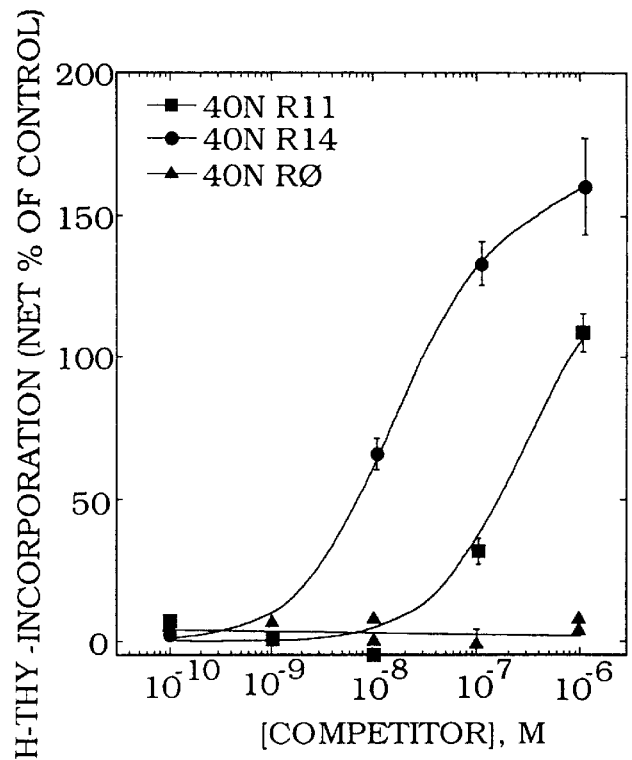
FIGS. 4A and 4B illustrate the results of the TGFβ1 bioassay on mink lung epithelial cells (MLEC).
Figure 4B:
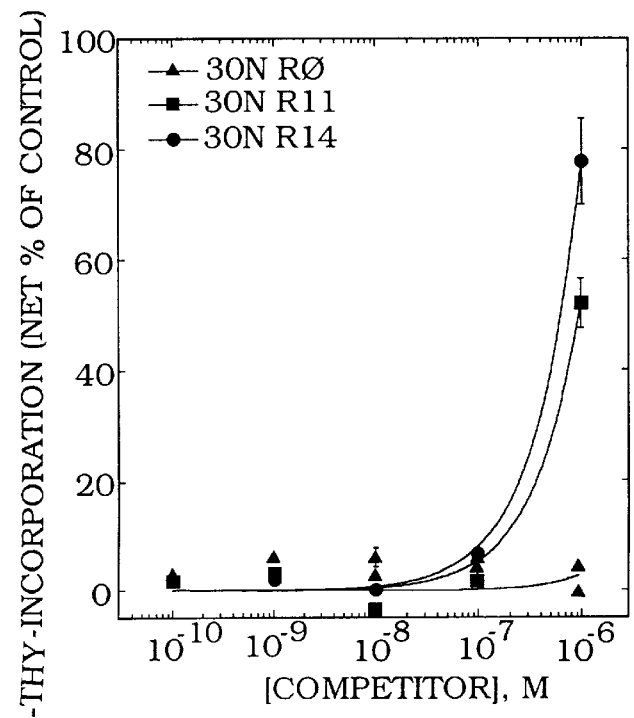
Figure 5A:
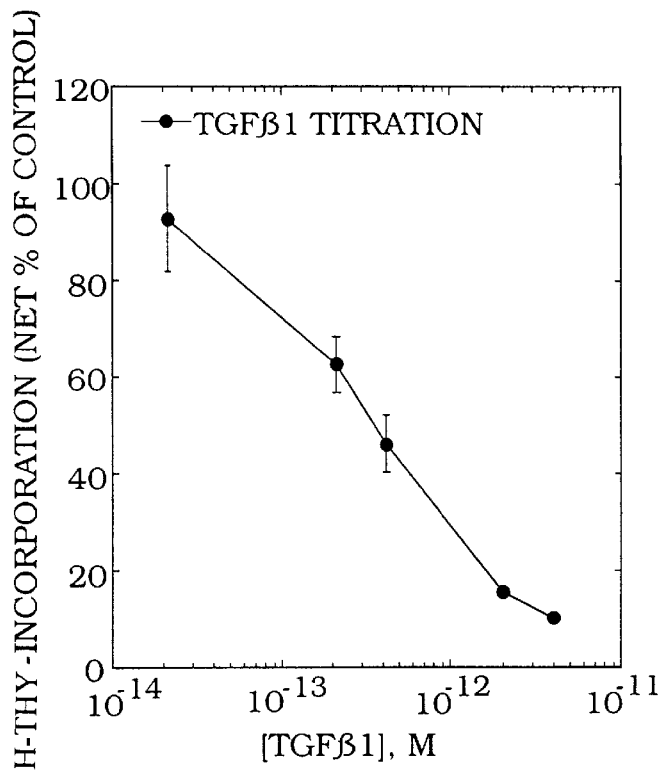
FIGS. 5A–5D illustrate the results of the TGFβ1 bioassay on mink lung epithelial cells (MLEC).
Figure 5B:
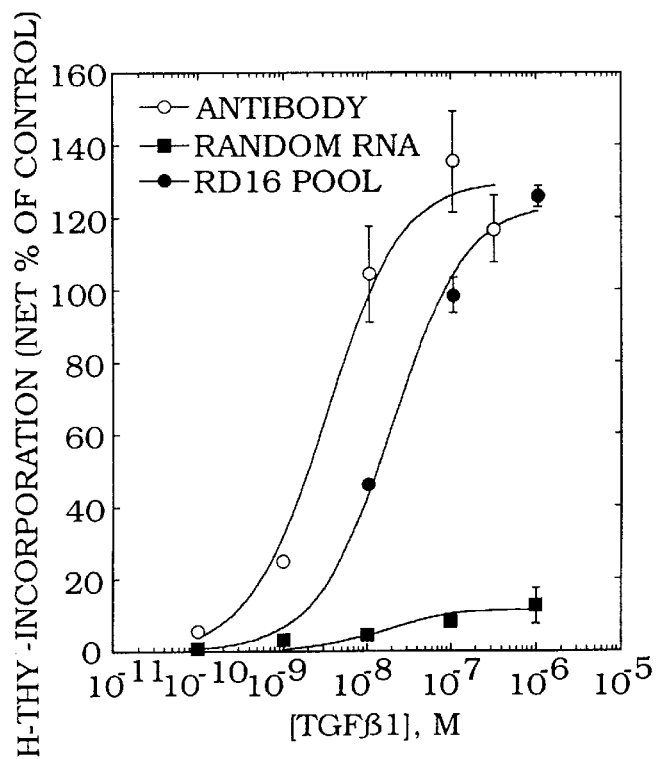
Figure 5C:
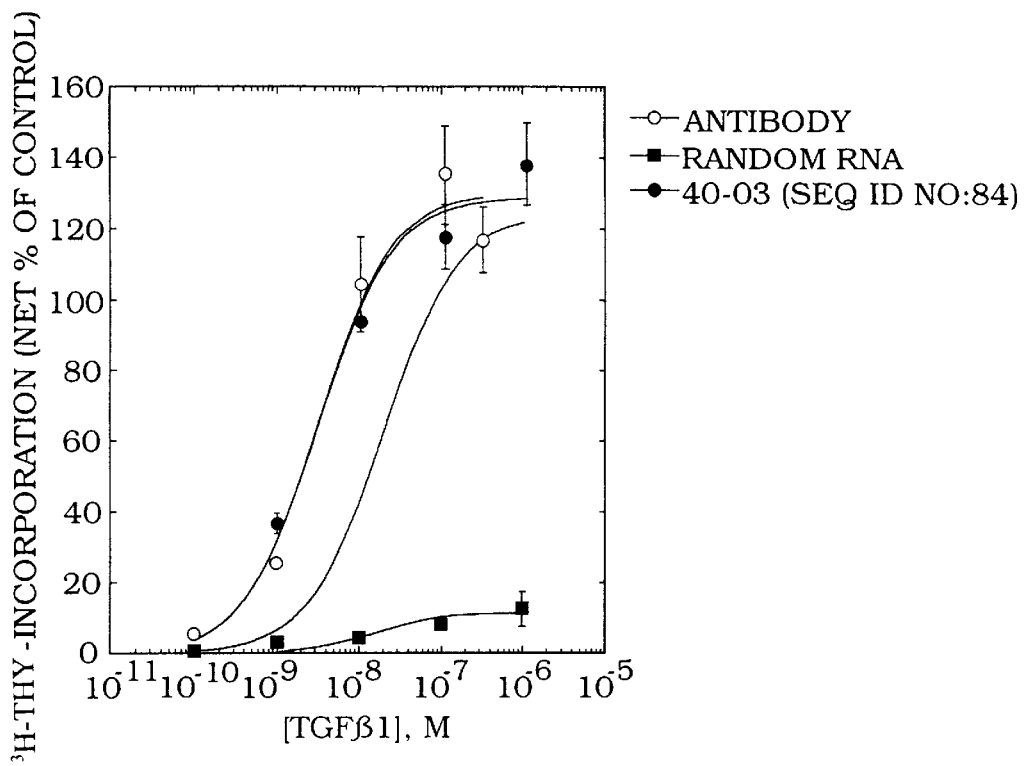
Figure 5D:
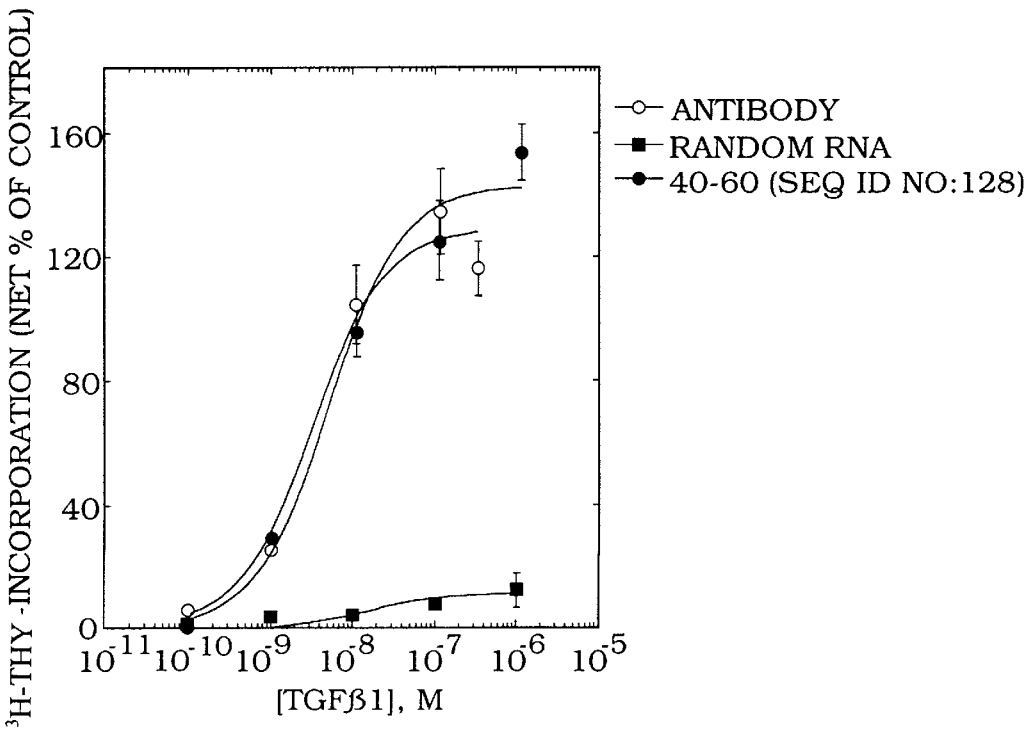

RNA from round 11 and 14 of the 40N and 30N pools along with random RNA controls were tested for TGFβ1 inhibitory activity using mink lung epithelial cells and measuring $^3$H-thymidine incorporation in the presence of 2 pM hTGFβ1. A significant hTGFβ1 inhibitory activity was observed with these advanced pools and not with random RNA (FIGS. 4A and 4B). It appears that the 40N round 14 pool was neutralizing serum-derived TGFβ1 in addition to the supplied TGFβ1 since the amount of DNA synthesis at high RNA concentrations is greater than that observed without exogenously added TGFβ1 (FIG. 4A).

Using the same MLEC assay several individual ligands were screened for TGFβ1 inhibitory activity. The results are summarized in Table 4 (Ki column). Several ligands were found that are good inhibitors of hTGFβ1. Typical results are shown in FIGS. 5A–5D. It seems that the majority of good inhibitors belong in class 1 which contains only ligands from the 40N (Table 4, Ki column), and as expected, the best bioactivity correlated with binding activity.

Figure 6:
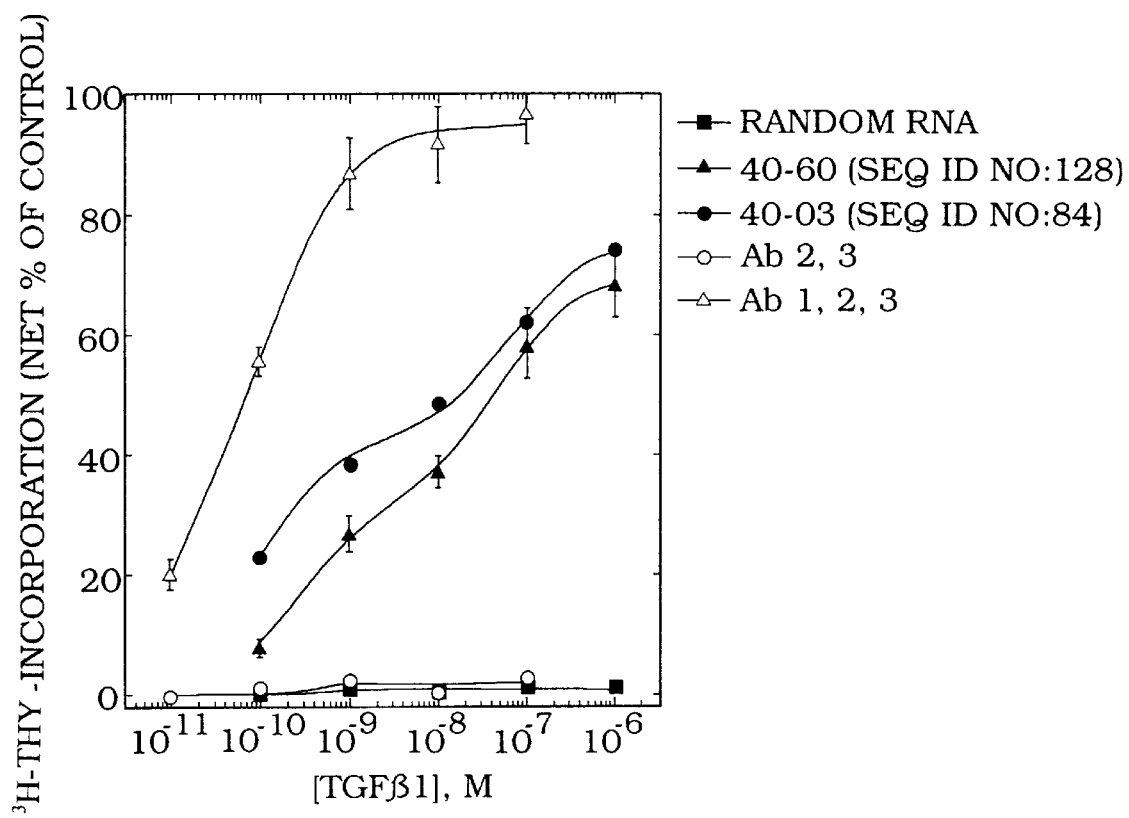
FIG. 6 shows the bioactivities of random RNA (■), ligand 40-60 (▲), ligand 40-03 (0), a monoclonal antibody specific for TGFβ2 and TGFβ3 (0) and a pan-specific antibody specific for TGFβ1, TGFβ2 and TGFβ3 (A), presented as $^3$H-thymidine incorporation as a per cent of control vs. concentration of TGFβ1.

TGFβ1 proteins of various species are highly conserved proteins. The human and mouse or rat TGFβ1 differ by a single amino acid. To determine the cross-species specificity, the ability of the TGFβ1 ligands to inhibit the murine (m)TGFβ1 bioactivity was tested. Since mTGFβ1 is not commercially available, conditioned media from mouse cells was used. Several cell lines were screened for TGFβ1 activity and it was found that 3T3 cells were the best source. FIG. 6 shows the specificity of conditioned media used and the ability of ligand 40-03 and 40-60 to inhibit the bioactivity of such conditioned media. Inhibition profiles with a pan-specific antibody (monoclonal mouse anti-TGFβ1/TGFβ2/TGFβ3 antibody; FIG. 6, open triangles) and a TGFβ2/TGFβ3 specific antibody (FIG. 6, open circles) demonstrate that the ability of the 3T3 conditioned media to inhibit the growth of MLEC is mainly due to TGFβ1. FIG. 6 also clearly demonstrates that, as expected, ligands 40-03 and 40-60 can inhibit the bioactivity of the 3T3 CM, presumably due to mTGFβ1.

Example 6

Effect of library random region length on the outcome of the SELEX

The above results suggest that size of the random region is important for the outcome of the SELEX process with TGFβ1 in terms of obtaining bioactive ligands. These data are summarized in Table 6. It appears that the 30N pool contained ligands that bind TGFβ1 with good affinities but these 30N ligands in general fail to inhibit the TGFβ1 bioactivity. The 20N pool failed to yield any TGFβ1 ligands. Only the 40N pool yielded ligands that bind TGFβ1 and inhibit its bioactivity.

Example 7

Proposed secondary structure of bioactive TGFβ1 Ligands

Figure 7:
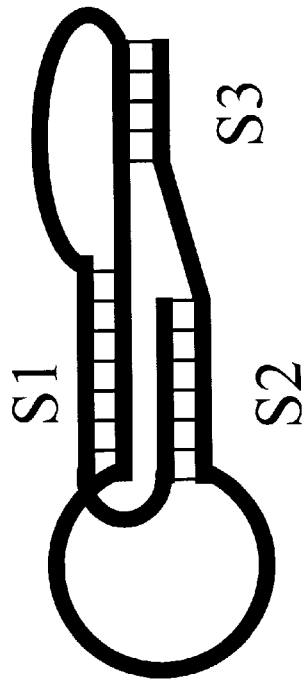
FIG. 7 is a proposed folding of the class 1 bioactive ligands. S1, S2 and S3 designate stem 1, stem 2 and stem 3 of the proposed structure.

The predicted common secondary structures among those ligands that could inhibit TGFβ1 bioactivity were investigated. These ligands appear to accommodate the proposed structure shown in FIG. 7 which is a double pseudoknot. This structure is consistent with enzymatic digestion results obtained with three bioactive class 1 ligands. Such enzymatic digestion confirmed stem 1 and stem 2 while stem 3 was postulated on the basis of truncation results.

TABLE 1

```
Starting ssDNA templates
40N7:
5'GGGAGGACGATGCGG[-40N-]CAGACGACTCGCCCGA 3'        SEQ ID NO: 1

30N7:
5'GGGAGGACGATGCGG[-30N-]CAGACGACTCGCCCGA 3'        SEQ ID NO: 2

20N7:
5'GGGAGGACGATGCGG[-20N-]CAGACGACTCGCCCGA 3'        SEQ ID NO: 3

SELEX PCR Primers:

5G7:
5'TAATACGACTCACTATAGGGAGGACGATGCGG 3'              SEQ ID NO: 4

3G7:
5'TCGGGCGAGTCGTCTG 3'                              SEQ ID NO: 5
```

TABLE 2

TGFβ1 SELEX conditions and results

| Round | [P]¹, nM | [R]², nM | % B³ | S/N⁴ | PF⁵ | PB⁶ | Spin⁷ | Bf. Wash⁸ | U. Wash⁹ |
|---|---|---|---|---|---|---|---|---|---|
| 40N | | | | | | | | | |
| 1A | 100 | 5000 | 0.42 | 13 | − | − | − | 5 | |
| 1B | 100 | 1000 | 0.60 | 30.7 | − | − | − | 5 | |
| 2 | 100 | 500 | 0.98 | 4.9 | + | − | − | 5 | |
| 3 | 100 | 500 | 3.40 | 2.6 | + | − | − | 10 | |
| 4 | 100 | 500 | 4.90 | 2.9 | + | − | − | 10 | |
| 5 | 33 | 167 | 2.50 | 1.9 | + | − | + | 10 | 5 |
| 6 | 33 | 167 | ND | ND | + | − | + | 10 | 55 |
| 7 | 11 | 56 | 1.00 | 8.0 | + | + | + | 10 | 55 |
| 8 | 11 | 56 | 0.40 | 5.0 | + | + | + | 10 | 55 |
| 9 | 3.3 | 16.5 | ND | 13.7 | + | + | + | 10 | 55 |
| 10 | 1.1 | 5.6 | 1.55 | 16.5 | + | + | + | 5 | 5 |
| 11 | 0.33 | 1.5 | 2.00 | 7.0 | + | + | + | 5 | 5 |
| 12* | 0.03 | 0.15 | 1.31 | 8.0 | + | + | + | 5 | 5 |
| 13* | 0.0033 | 0.016 | 0.33 | 2.4 | + | + | + | 5 | 5 |
| 14* | 0.011 | 0.055 | 1.00 | 3.5 | + | + | + | 5 | 5 |
| 15L | 0.033 | 0.0066 | 10.00 | 130.0 | + | + | + | 5 | 5 |
| 16L | 0.033 | 0.0066 | 11.50 | 345 | + | + | + | 5 | 5 |
| 30N | | | | | | | | | |
| 1A | 140 | 7000 | 0.36 | 4.4 | − | − | − | 5 | |
| 1B | 140 | 1400 | 1.80 | 20.9 | − | − | − | 5 | |
| 2 | 140 | 700 | 1.90 | 11.1 | + | − | − | 5 | |
| 3 | 140 | 700 | 4.60 | 4.4 | + | − | − | 10 | |
| 4 | 140 | 700 | 5.20 | 9.0 | + | − | − | 10 | |
| 5 | 5.0 | 25.6 | 1.50 | 4.3 | + | − | + | 10 | 5 |
| 6 | 11 | 55 | 0.70 | 2.6 | + | − | + | 10 | 55 |
| 7 | 3.3 | 16.5 | 0.26 | 1.7 | + | + | + | 10 | 55 |
| 8 | 3.3 | 16.5 | 0.10 | 2.0 | + | + | + | 10 | 55 |
| 9 | 3.3 | 16.5 | ND | 14.4 | + | + | + | 10 | 55 |
| 10 | 1.1 | 5.6 | 0.39 | 4.5 | + | + | + | 5 | 5 |
| 11 | 0.33 | 1.5 | 0.38 | 4.0 | + | + | + | 5 | 5 |
| 12* | 0.03 | .15 | 0.40 | 3.0 | + | + | + | 5 | 5 |
| 13* | 0.03 | .16 | 0.49 | 3.0 | + | + | + | 5 | 5 |
| 14 | 0.11 | .55 | 0.90 | 10.0 | + | + | + | 5 | 5 |
| 15 | 0.033 | 0.165 | 0.50 | 6.7 | + | + | + | 5 | 5 |
| 16L | 0.11 | .022 | 1.8 | 25.7 | + | + | + | 5 | 5 |
| 17L | 0.033 | 0.0066 | 1.5 | 13.6 | + | + | + | 5 | 5 |
| 20N | | | | | | | | | |
| 1A | 1000 | 50000 | 0.54 | 15.8 | − | − | − | 5 | |
| 1B | 100 | 1000 | 1.70 | 39.5 | − | − | − | 5 | |
| 1C | 1000 | 5000 | 3.80 | 51.0 | − | − | − | 5 | |
| 2 | 1000 | 5000 | 3.70 | 72.5 | + | − | − | 5 | |
| 3 | 1000 | 5000 | 5.90 | 122.0 | + | − | − | 10 | |
| 4 | 330 | 1670 | 1.70 | 17.4 | + | − | − | 10 | |
| 5 | 4.0 | 20.6 | 1.00 | 10.6 | + | − | + | 10 | 5 |
| 6 | 1.2 | 6.1 | 0.60 | 4.7 | + | − | + | 10 | 10 |
| 7 | 3.3 | 16.5 | 0.06 | 3.0 | + | + | + | 10 | 55 |
| 8 | 3.3 | 16.5 | 0.30 | 15 | + | + | + | 10 | 55 |
| 9 | 3.3 | 16.5 | ND | 6.6 | + | + | + | 10 | 55 |

TABLE 2-continued

TGFβ1 SELEX conditions and results

| Round | [P]¹, nM | [R]², nM | % B³ | S/N⁴ | PF⁵ | PB⁶ | Spin⁷ | Bf. Wash⁸ | U. Wash⁹ |
|---|---|---|---|---|---|---|---|---|---|
| 10 | 3.3 | 16.5 | 0.31 | 16.5 | + | + | + | 5 | 5 |
| 11 | 1.1 | 5.6 | 0.19 | 4.0 | + | + | + | 5 | 5 |
| 12 | 1.1 | 5.6 | 1.2 | 13.0 | + | + | + | 5 | 5 |
| 13L | 0.1 | 0.022 | 0.9 | 10.0 | + | + | + | 5 | 5 |

[1]Protein concentration in nanomolar
[2]RNA concentration in nanomolar
[3]Backround expressed as % of input
[4]Signal to noise
[5]Use of nitrocellulose prefiltered RNA
[6]Use of preblocked nitrocellulose with BSA
[7]Spinning of binding reactions before filtering through nitrocellulose
[8]Volume in ml of buffer wash
[9]Volume in ml of 0.5 M urea wash
[10]L indicates RNA limiting SELEX conditions
[11]The RNA pool used was a mixture of 2–3 pools obtained from 3 fold serial dilutions of a binding reactions. Only the most stringent condition is shown.

TABLE 3

Sequence of individual TGFβ1 RNA ligands. The sequences of the fixed regions (Table 1) are not shown.

| | | SEQ ID NO: |
|---|---|---|
| 20-01 | GUCUAUUUUUGCCUCCUCCC | 6 |
| 20-02 | AAUCCUUUCUUAAACCUCCC | 7 |
| 20-03 | UGUCUUUAGCUUAGGUUAUUCCUUCUGCCG | 8 |
| 20-04 | UGUCUUUAGCUUAGGUGAUUCCUUCUGCCG | 9 |
| 20-05 | UGUCUCUACCUUAGGUUGAUUCCUUCUACCG | 10 |
| 20-06 | UGAGUCUUGUUUUUUCGUC | 11 |
| 20-07 | UUGGCAUUGAAAGAGCUGGCAUACAUUCGC | 12 |
| 20-08 | UCCUUUCUAACAUUCCUCCC | 13 |
| 20-09 | GUCGUUGUUUUUCUCCUCCC | 14 |
| 20-10 | UGAGUCUUUCUUUUCGUCCC | 15 |
| 20-11 | GUCGUUUUUUUGGUCCUC | 16 |
| 20-12 | GUUUUUAUUAUUCGUUUGGC | 17 |
| 20-14 | GUCGAUCAUUUUUAGCCUCCC | 18 |
| 20-17 | UGAGUUGAUCUUUUCGUCCC | 19 |
| 20-18 | UGCCUUUAGCUUAGGCAUUGCCUUCUGUG | 20 |
| 20-19 | CAAAAUUUUUGGUCAAGCCGUCAUUGCCGC | 21 |
| 20-21 | GUCGUUCUUUUUUCCCUCCC | 22 |
| 20-23 | AAUUUUUGUGAAGACGUUUGCCGCUUUGCC | 23 |
| 20-24 | CGCAUCUUCUGUUUUCUCCC | 24 |
| 20-25 | GGAAUUUUUGGUAAAGCCGUAUGCCUCGC | 25 |
| 20-26 | UCAUCUCUGGGAGUUAAGAUCAUUUGGCCG | 26 |
| 20-27 | GCAGCCUCUGAUUUUCUCCC | 27 |
| 20-28 | GUCGUGAUUUUCGUUCUGCC | 28 |
| 20-29 | GUCGUAUUUUUUCCGCCUCCC | 29 |

TABLE 3-continued

Sequence of individual TGFβ1 RNA ligands. The sequences of the fixed regions (Table 1) are not shown.

| | | SEQ ID NO: |
|---|---|---|
| 20-31 | UCCUCAGCCUCUCACUUAUUAUCCUCCC | 30 |
| 20-34 | GUCUACUUGUUUUACCUCCC | 31 |
| 20-35 | CGAUUUUUCGUCUUUUGGC | 32 |
| 20-36 | UGUCUAUAGCCUUGAUUAUAUCAUCUGCCG | 33 |
| 20-37 | CGAUUCCUCUUUUCACUCCC | 34 |
| 20-38 | UCCCAUUUUCUCCUCUCCC | 35 |
| 20-40 | GUUAAUUUUUGUCCUCUGGC | 36 |
| 20-41 | UUUUUUUCUUUUUUCUUUUUUUCCG | 37 |
| 20-42 | UCGUCUUUGUUUUUCUCCC | 38 |
| 20-43 | UGUCUAUAGCCUUGAUUACAUCUGCCG | 39 |
| 20-45 | UGCCUUUAGCUUAGGCAUUGCCUUCUGCCG | 40 |
| 20-46 | UGUCUAUAGCUUGAUUUUUAAUUUCUGCCG | 41 |
| 20-47 | UUUUAUUUUCUUCGUCUGGC | 42 |
| 20-48 | GAUGAACCGAACCGAGGUUAAGGUGCCAGAGUAGACGCUCAU | 43 |
| 20-49 | UCGUCUAUUUUUUCCCUCCC | 44 |
| 20-50 | CUUUCGUCUGUUUUCCUGCC | 45 |
| 30-01,07,18,23 | UGUCUUUAGCCUAGGUGAUUCCUUCUGCCG | 46 |
| 30-02 | CCUUGUUUUCUUUUUUCUUUUUUCACCCC | 47 |
| 30-03 | UGUCUUUAGCCCAGGUGAUUCCUUCUGCCG | 48 |
| 30-04 | UUAACCGUAAAGACGGCAUGAUGUAGUCCG | 49 |
| 30-05 | UUUUUUUAGCUUAGGUGAUUCCUUCNNCCU | 50 |
| 30-06 | UGCCUUUAGCUUAGGCUUUGCCUUCUGCCG | 51 |
| 30-08 | CGGAAUUUUUGUUGAGCCGUAUGCCGC | 52 |
| 30-09,42 | UGCCUUUAGCUUAGGUGAUUCCUUCUGCCG | 53 |
| 30-10 | UGUCUUUAGCCUAGGUGAUUCCUUCUGCCG | 54 |
| 30-12,24,21,40,41 | UGUCUAUAGCCUGAUUUUUAAUCUCUGCCG | 55 |
| 30-15 | UUGACCGUUAAGACGGCAUGAUGUGGUCCG | 56 |
| 30-16,27,38,46 | UGCCUUUAGCUUAGGCAUUGCCUUCUGCCG | 57 |
| 30-17 | UGCCUUUAGCUUAGGCUUUGCCUUCUGCCG | 58 |
| 30-19 | UUAACCNUAAAAUACGGCUUGANUUCUUCCG | 59 |
| 30-20 | UGCCUUUAGCUUAGGCAUUGCCUUCUGCCG | 60 |
| 30-22 | UUAACCGUAAAGACGGCAUGAUGUUUUCCG | 61 |
| 30-25 | UUGGCAUUGAAAGAGGCGUCAUAUGUUCGC | 62 |
| 30-26 | CCUUUCUUUCUUUUUAUUUUCUUCCCCUCCC | 63 |
| 30-28 | UGCCUUUAGCCUAGACCUUGUCUUCUGCCG | 64 |
| 30-29 | UGUCUUUAGCCUAGGUGAUUCCUUCUGCCG | 65 |
| 30-30 | UGUCUUUAGCCUAGGUGAUUCCUUCUGCCG | 66 |

TABLE 3-continued

Sequence of individual TGFβ1 RNA ligands. The sequences of the fixed regions (Table 1) are not shown.

| | | SEQ ID NO: |
|---|---|---|
| 30-31 | ACCGGUAAGGGCACUGCAGGAACACAAUCCCCUAUGCGAC | 67 |
| 30-32 | GGAAUUUUUGGUAAAGCCGUAUGCCUCGC | 68 |
| 30-33 | UGGCAUUGAAAGAGAUCGCAUACCUUCGC | 69 |
| 30-34 | UGUCUAUAGCCUUGAUUACAUCAUCUGCCU | 70 |
| 30-35 | UGUCUUUAGCCUAGGUGAUUCCUUCUGCCU | 71 |
| 30-14 | UGCCUUUAGCUUAUGCAUUGCCUUCUGCCG | 72 |
| 30-36 | UGCCUUUAGCUAGGCAUUCGCCUUCUGCCG | 73 |
| 30-37 | UGUCUUUGGCCUAGGUGAUUCCUUCUGCCG | 74 |
| 30-39 | UGUCUUUAGCUUAGGUGAUUCCUUCUGCCG | 75 |
| 30-43 | UGUCUUUAGCCUAGGUGAUUCCUUCUGCCG | 76 |
| 30-44 | UGCCUUUAGCUUAGGCAUUGCCUUGCCG | 77 |
| 30-45 | GGUCUUUUAUUUUUGUUUUUCUCUGUGCCC | 78 |
| 30-47 | UUAACCGUAAAGACAGCAUGAUGUAGUCUG | 79 |
| 30-48 | UUUUUUUCUUUUCCUUCCUUUUCUUACCG | 80 |
| 30-49 | UUAACCGUAAAGACGGCAUGAUGUUGUCCG | 81 |
| 30-50 | GGAAUUUUUGGUAAAGCCGUAUGCCUCGC | 82 |
| 40-02 | GCCAAGGUUACGCCGUCGGACCCUGCUGCCAACAUCCUCCC | 83 |
| 40-03 | GGGUUAUUGGGCGUCAACAUCCCCGAUUCUUUUCACGUC | 84 |
| 40-04 | AUGCCUUUUGCCUUCAGGGUGUAAUUCCUUGAUCUGUCCG | 85 |
| 40-05 | AACAAGGUUACGCCGUCGGACCCUGCUGCCAACAUCCUCCC | 86 |
| 40-06 | UUAGGGGCGUCAACACCGCUAUCAUAAUUUUCGCCUUCCC | 87 |
| 40-08 | CGCAAGGUUACGCCGUCGGACCCUGCUGCCAACAUCCUCC | 88 |
| 40-11 | UGCCUUUAGUCUGAAUCUUCUACCAUGAUUCUCUGCCG | 89 |
| 40-12 | GACCCUUGUCUGCGAUUCAACUCGUAGGUUUUCUCACGUG | 90 |
| 40-13 | AGCAAGGUUACGAGGUCGGACCCUGCUGCCAACAUCCUCCC | 91 |
| 40-14 | CAUUAUGGCGUCAACAUGCCGGUUUUCGAUUCUCAUUGUC | 92 |
| 40-15 | CUCUAACUUCUUUUUCGCCUGUGUGUUUUCUUUUUGCUG | 93 |
| 40-16 | UUAGGGGCGUCAACACCGCUAUUACAUCUUUCGCCUCCC | 94 |
| 40-17 | GGUCGUUUUGUUUUUGUUUUUUGUAGCCCGGUCAUCCC | 95 |
| 40-19 | UUAGCGCGAGUUCAACACCGCAUGUGAUUCUUUCGCCUCC | 96 |
| 40-20 | UACAAGGUUACGCCGUCGGACCCUGCUGCCAACAUCCUCCC | 97 |
| 40-21,34 | GACCCUUGUCUGCGAUUCAACUCGUAGGUCUUCUCACGUG | 98 |
| 40-22,35 | UUAGGGGCGUCAACACCGCUAUUACAAUUUCGCUUCC | 99 |
| 40-23 | UUAGGGGCGUCAACACCGCUAUUACAAUCUUCGCUUCC | 100 |
| 40-24 | UUAUGGGCGUCAACACCGCUAUUACAACUUUCGCUUUCC | 101 |
| 40-25 | UGUCGAUCGUUUGCUGUUUGAUUUCUUUUGUCCCUCCCGUG | 102 |
| 40-26 | UUAGGGGCGUCAACAUCGCUAUUACAAUCUUCGCCUUCC | 103 |

TABLE 3-continued

Sequence of individual TGFβ1 RNA ligands. The sequences of the fixed regions (Table 1) are not shown.

| | | SEQ ID NO: |
|---|---|---|
| 40-28 | UUAGGGGCGUCAACACCGCUAUUACAACUUUCGCCUCAC | 104 |
| 40-29 | GACCCUUUUCUGCGAUUCAACUCGUACGUCUUCUCACGUG | 105 |
| 40-31 | UUAAGGGCGUCAACACCGCUAUUACAACUUUCGCUUCC | 106 |
| 40-32 | UUAUGGGCGUCAACACCGCUAUUACAACUUUCGCCUC | 107 |
| 40-33 | AGCAAGGUUACGCCGUCGGACCCUGCUGCCAACAUCCUCCC | 108 |
| 40-36 | GUCAAGGUUACGCCGUCGGACCCUACUGCCCC | 109 |
| 40-37 | CUCCUAUAUUCAUGUUAUUGUUUUUUUCUUCCAGCUUGCCC | 110 |
| 40-38 | AGAUAAUUAUCAGCGGUGGACGGGGUGCCGGUACUGCCGC | 111 |
| 40-39 | UGCCUUUAGCCUAAGUUGAUCUAUUCAGCUUUCUGCCG | 112 |
| 40-40 | CCCAAGGUUACGCCGUCGGACCCUACUGCCAACUUCCUCCC | 113 |
| 40-41 | UGCCUUUAGCCUGAGUAUACUGAUGUAUAUUCUCUGCCG | 114 |
| 40-42 | UAGCGCGAGUUCAACACCGCAUGUGACUCUUUCGCCUCC | 115 |
| 40-43 | AUCCUUUUUUUAGCUUUUUUCUUUUUCCUGCCCCACUUCCC | 116 |
| 40-44 | UGCAAGGUUACGCCGUCGGACCCUGCUGCCAACAUCCUCCC | 117 |
| 40-45 | GGGCUUUUCCUUUAGUACUUUUUUGUUUCGCUCCCCCC | 118 |
| 40-51 | UGCCUUUAGUCUGAAUCUUACCAUGCGAUUUUCUGCCG | 119 |
| 40-52 | AACAAGGUUACUCCGUCGGACCCUGCUGCCAACAUCCUCCC | 120 |
| 40-53 | GACUCUUGUCUGCGAUUCAACUCGUAGGUCUUCUCACGUG | 121 |
| 40-54 | UUAGGGGCGUCAACACCGCUAUCAUAACUUUCGCUUCCC | 122 |
| 40-55 | UUAGGGGCGUCAACACCGCUAUUCAACCUUCGCUUCCC | 123 |
| 40-56 | UUAGGGCGUCAACACCGCUAUUACAACUUUCGCCUCCC | 124 |
| 40-57 | GGUGUCGUCUUUCAACCCCU | 125 |
| 40-58 | UUAUGGGCGUCAACACCGCUAUUACAACUUUCGCCUCCC | 126 |
| 40-59 | CCCAAGGUUACGCCGUCGGACCCUGCUGCAAACAUCCUCCC | 127 |
| 40-60 | UUAUGGGCGUCAACACCGCUAUUACAGUUUUCGCCUCCCC | 128 |
| 40-61,76 | UUAGGGGCGUCAACACCGCUAUUACAAUCUUCGCUUUCC | 129 |
| 40-62 | GCCAAGGUUACGCCGUCGGACCCUGCUGCCAACAUCUUCCC | 130 |
| 40-64 | UUAGGGGCGUCAACACCGCUAUUACAAUCUUCGUCUUCC | 131 |
| 40-65 | GUCAAGUUUACGCCGUCGGACCCUGCUGCCAACAUCCUCCC | 132 |
| 40-66 | UUCAAGGUUACGCCGUCGGACCCUGCUGCCAACAUCCUCCC | 133 |
| 40-67 | CUCAAGGUUACGCCGUCGGACCCUGCUGCCAACAUCCUCCC | 134 |
| 40-68 | UUAGGGCUUCAACACCGCUAUUACAUUCUUCGCCUCCC | 135 |
| 40-69 | CACAAAGUUACGCCGUAGGACCCUGCUGCCAACAUCCUCCC | 136 |
| 40-70 | GGAUGGUCAGUUUCGGUUUUUCAUAUGUUUAUUUUCCCCCC | 137 |

TABLE 3-continued

Sequence of individual TGFβ1 RNA ligands. The sequences of the fixed regions (Table 1) are not shown.

| | | SEQ ID NO: |
|---|---|---|
| 40-71 | UAUUGACUUUUGUUUCUUUUUCUUUGCCUGGUCCC | 138 |
| 40-72 | UUAGGGGCGUCAACACCGCUAUUACAACUUUCGCUUCCC | 139 |
| 40-73 | CUUCUUUUCUUCUUUUCUUUAUGUCUUCUUCAUGCCG | 140 |
| 40-75 | GACCNUUGUNUGCGAUUCAACUCGUAGGUCUUCUCACGUG | 141 |
| 40-77 | UUAUGGGCGUCAACACCGCUAUUACAACUUUCGCCCCC | 142 |
| 40-79 | UUAUGGGUGUCAACACCGCUAUUACAACUUUCGCCUCCC | 143 |

TABLE 4

Proposed alignment and observed affinity and bioactivity of TGFβ1 ligans. The sequences of the fixed region (Table 1) are not shown.

| | | Kd1 (nM) | Kd2(pM) | P1 (%) | P2 (%) | P2/P1 (%) | BCG (%) | Ki, nM |
|---|---|---|---|---|---|---|---|---|
| Class 1 | | | | | | | | |
| 40-03 | GGGUUA UUGGGGCUCAACAUCCCGAU UCUUUUCA CGUC | 4.6 ± 1.1 | 0.3 ± 0.08 | 60.3 | 24.4 | 40.5 | | 0.4 |
| 40-06 | GGGGCGUCAACACCGCU AU CAUAAUUUU CGCCUUCCC | 3.7 ± 0.6 | 1.6 ± 0.6 | 60.0 | 10.0 | | 16.7 | |
| 40-14 | CAUUA UGCCCUCAACAU GCCGGUUUUCGAUUCUCAUUGUC | 5.7 ± 1.4 | 0.4 ± 0.2 | 62.9 | 12.1 | 19.2 | | 3.9 |
| 40-16 | UUA GGGGCUCAACACCGCU AU UACA UCUUU CGCCUCCC | 1.7 ± 0.6 | 0.06 ± 0.04 | 48.5 | 32.8 | 67.6 | | 0.6 |
| 40-19 | UUAGCCCGAGUCAACACCGC AU GUGAUUCUUU CGCCUCC | 4.2 ± 2.2 | 3.7 ± 2.7 | 68.0 | 21.5 | 31.6 | | 28.0 |
| 40-22,35 | UUA GGGGCCUCAACACCGCU AU UACAAUUUU CGCUCC | 13.9 ± 4.3 | 17.6 ± 4.5 | 93.8 | 13.3 | 14.2 | | |
| 40-23 | UUA GGGGCCUCAACACCGCU AU UACAAUCUU CGCUCC | 14.2 ± 4.5 | 15.6 ± 4.0 | 58.2 | 13.1 | 22.5 | | 0.75 |
| 40-24 | UUA UGGGGCCUCAACACCGCU AU UACAAUCUU CGCUUCC | 12.7 ± 4.7 | 27.5 ± 10.2 | 100 | 12.4 | 12.4 | | |
| 40-26 | UUA GGGGCCUCAACAUCGCU AU UACAAUCUU CGCCUUCC | 7.7 ± 1.6 | 40.8 ± 23.3 | 73.7 | 8.4 | 11.4 | | |
| 40-28 | UUA GGGGCCUCAACACCGCU AU UACAAUCUU CGCCUCAC | 12.3 ± 2.4 | 81.6 ± 47.2 | 93.4 | 4.8 | 5.1 | | |
| 40-31 | UUA AGGGCCUCAACACCGCU AU UACAACUUU CGCUUCC | 8.4 ± 2.8 | 0.7 ± 0.4 | 34.4 | 9.3 | 27.0 | | 2.56 |
| 40-32 | UUA UGGGCCUCAACACCGCU AU UACAACUUU CGCUC | 14.0 ± 6.4 | 5.0 ± 3.3 | 51.1 | 7.7 | 15.0 | | |
| 40-42 | UAGCCGAGUCAACACCGC AU GUGACUCUUU CGCCUCC | 11.4 ± 1.9 | 0.09 | 37.9 | 6.2 | 16.3 | | |
| 40-54 | UUA GGGGCCUCAACACCGCU AU CAUAACUUU CCGCUUCCC | 8.5 ± 1.8 | 6.75 ± 9 | 46.7 | 25.9 | 55.5 | | |
| 40-55 | UUA GGGGCCUCAACACCGCU AU U CAACCUU CGCUUCC | 8.0 ± 2.5 | 0.1 ± 0.06 | 64.9 | 24.8 | 38.2 | | 2.9 |
| 40-56 | UUA GGGGCCUCAACACCGCU AU UACAACUUU CGCCUCCC | 4.2 ± 1.3 | 0.2 | 41.0 | 12.3 | 30.0 | | 7.4 |
| 40-58 | UUA GGGGCCUCAACACCGCU AU UACAACUUU CGCCUCC | 4.4 ± 1.6 | 5.3 ± 2.2 | 35.1 | 24.6 | 70.0 | | 0.9 |
| 40-60 | UUA UGGGCCUCAACACCGCU AU UACAAGUUU CGCCUCCC | 3.8 ± 1.5 | 1.9 ± 0.8 | 32.5 | 25.5 | 78.5 | | 0.8 |
| 40-61,76 | UUA GGGGCCUCAACACCGCU AU UACAAUCUU CGCUUCC | 13.5 ± 4.2 | 1.0 ± 0.8 | 56.5 | 4.9 | 8.6 | | |
| 40-64 | UUA GGGGCCUCAACACCGCU AU UACAAUCUU CGUCUUCC | 5.6 ± 2.0 | 3.1 ± 1.8 | 37.0 | 15.3 | 41.3 | | |
| 40-68 | UUA GGGGCUUCAACACCGCU AU UACAAUUCUU CGCCUUCC | 20.7 ± 3.2 | 0.4 ± 0.3 | 62.9 | 1.9 | 3.0 | | |
| 40-72 | UUA GGGGCCUCAACACCGCU AU UACAACUUU CGCUUCCC | 1.4 ± 0.8 | 0.07 ± 0.05 | 23.8 | 42.4 | ? | | |
| 40-77 | UUA UGGGCCUCAACACCGCU AU UACAACUUU CGCCCCC | 3.7 ± 1.5 | 1.73 ± 1.43 | 27.0 | 16.3 | 60.4 | | |

TABLE 4-continued

Proposed alignment and observed affinity and bioactivity of TGFβ1 ligans. The sequences of the fixed region (Table 1) are not shown.

| | | Kd1 (nM) | Kd2(pM) | P1 (%) | P2 (%) | P2/P1 (%) | BCG (%) | Ki, nM |
|---|---|---|---|---|---|---|---|---|
| 40-79 | UUA UGGGUGUCAACACCGCU AU UACAACUUU CGCCUCCC | 0.6 ± 0.1 | 0.5 ± 0.4 | 18.5 | 12.23 | 66 | | |
| Class 2 | | | | | | | | |
| 40-02 | GCCAAGGUUACGCCGUCGGACCCUGCUGCCAACAUCCUCCC | 14.8 ± 1.4 | | 100 | | | | |
| 40-05 | AACAAGGUUACGCCGUCGGACCCUGCUGCCAACAUCCUCCC | 12.6 ± | | 100 | | | | |
| 40-08 | CGCAAGGUUACGCCGUCGGACCCUGCUGCCAACAUCCUCC | 15.4 ± 1.6 | | 82 | | | | |
| 40-13 | AGCAAGGUUACGAGGUCGGACCCUGCUGCCAACAUCCUCCC | 15.4 ± 9.6 | | 100 | | | | |
| 40-20 | UACAAGGUUACGCCGUCGGACCCUGCUGCCAACAUCCUCCC | 11.2 ± 7.8 | | 100 | | | | >1300 |
| 40-33 | AGCAAGGUUACGCCGUCGGACCCUGCUGCCAACAUCCUCCC | 26.6 ± 14 | | 100 | | | | |
| 40-36 | GUCAAGGUUACGCCGUCGGACCCUACUGCCCC | 41.7 ± 9.5 | | 99 | | | | |
| 40-40 | CCCAAGGUUACGCCGUCGGACCCUACUGCCAACUUCCUCCC | 18 ± 2.8 | | 91.3 | | | | |
| 40-44 | UGCAAGGUUACGCCGUCGGACCCUGCUGCCAACAUCCUCCC | 11.1 ± 0.8 | | 60.44 | | | | |
| 40-52 | AACAAGGUUACGCCGUCGGACCCUGCUGCCAACAUCCUCCC | | | | | | | |
| 40-59 | CCCAAGGUUACGCCGUCGGACCCUGCUGCAAACAUCCUCCC | | | | | | | |
| 40-62 | GCCAAGGUUACGCCGUCGGACCCUGCUGCCAACAUCUUCCC | | | | | | | |
| 40-65 | GUCAAGUUUACGCCGUCGGACCCUGCUGCCAACAUCCUCCC | | | | | | | |
| 40-66 | UUCAAGGUUACGCCGUCGGACCCUGCUGCCAACAUCCUCCC | | | | | | | |
| 40-67 | CUCAAGGUUACGCCGUCGGACCCUGCUGCCAACAUCCUCCC | | | | | | | |
| 40-69 | CACAAAGUUACGCCGUAGGACCCUGCUGCCAACAUCCUCCC | | | | | | | |
| Class 3 | | | | | | | | |
| 40-12 | GACCCUUGUCUGCGAUUCAACUCGUAGGUUUUCUCACGUG | 5.5 ± 0.7 | 0.7 ± 0.2 | 64.7 | 10.0 | 15.5 | | 6.88 |
| 40-21,34 | GACCCUUGUCUGCGAUUCAACUCGUAGGUCUUCUCACGUG | 10.1 ± 3.5 | 6.5 ± 4.0 | 100 | 9.3 | 9.3 | | 1.68 |
| 40-29 | GACCCUUUUCUGCGAUUCAACUCGUACGUCUUCUCACGUG | 10.9 ± 5.5 | | 100 | | | | |
| 40-53 | GACUCUUGUCUGCGAUUCAACUCGUAGGUCUUCUCACGUG | | | | | | >1300 | |
| 40-75 | GACCNUUGUNUGCGAUUCAACUCGUAGGUCUUCUCACGUG | | | | | | 2.25 | |

TABLE 4-continued

Proposed alignment and observed affinity and bioactivity of TGFβ1 ligans. The sequences of the fixed region (Table 1) are not shown.

| | | | Kd1 (nM) | Kd2 (pM) | P1 (%) | P2 (%) | P2/P1 (%) | BCG (%) | Ki, nM |
|---|---|---|---|---|---|---|---|---|---|
| Class 4 | | | | | | | | | |
| 20-03 | UGUCUUUAGCUUAGG | UUAUUCCU UCUGCCG | 0.11 ± 0.1 | 0.3 ± 1.7 | 9.3 | 13.4 | | | |
| 20-04 | UGUCUUUAGCUUAGG | UGAUUCCU UCUGCCG | 0.2 | | 8.0 | | | | |
| 20-05 | UGUCUCUACCUUAGG | UUUAUUCCU UCUACCG | 0.11 ± 0.1 | | 10.49 | | | | |
| 20-18 | UGCCUUUAGCUUAGG | CAUUGCC UUCUGUG | | | | | | | |
| 20-36 | UGUCUAUAGCCUUGA | UUAUACCA UCUGCCG | | | | | | | |
| 20-43 | UGUCUAUAGCCUUGA | UUACAUCA UCUGCCG | | | | | | | |
| 20-45 | UGCCUUUAGCUUAGG | CAUUGCCU UCUGCCG | | | | | | | |
| 20-46 | UGUCUAUAGCUUGAU | UUUUAAUU UCUGCCG | | | | | | | |
| 30-01,07, 18,23 | UGUCUUUAGCCUAGG | UGAUUCCU UCUGCCG | 3.4 | | 6.3 | | | | |
| 30-03 | UGUCUUUAGCCCAGG | UGAUUCCU UCUGCCG | 58.2 | 262 | ~100 | 1.2 | | | |
| 30-05 | UUUUUUUAGCUUAGG | UGAUUCCU UCNNCCU | 100 | | | | | | |
| 30-06 | UGCCUUUAGCUUAGG | CUUUGCCU UCUGCCG | 56.6 | 74.1 | ~100 | 2.4 | | | |
| 30-09, 42 | UGCCUUUAGCUUAGG | UGAUUCCU UCUGCCG | 5.35 ± 0.9 | | 22.7 | | | | |
| 30-10 | UGUCUUUAGCUUAGG | UGAUUCCU UCUGCCG | 4.05 ± 1.5 | 75.5 | 28.6 | 17.9 | 62.6 | | >300 |
| 30-12,24, 21,40,41 | UGUCUAUAGCCUGAU | UUUUAAUC UCUGCCG | 2.82 ± 1.7 | 60.8 | 24.8 | 23.2 | 93.5 | | |
| 30-14 | UGCCUUUAGCUUAGG | CAUUGCCU UCUGCCG | | | | | | | |
| 30-16,27, 38,46 | UGCCUUUAGCUUAGG | CAUUGCCU UCUGCCG | 71.8 | 211 ± 90 | 99.8 | 4.3 | ~4 | | |
| 30-17 | UGCCUUUAGCUUAGG | CUUUGCCU UCUGCCG | 67 | 205 ± 93 | 99.9 | 4.3 | ~4 | | |
| 30-20 | UGCCUUUAGCUUAGG | CAUUGCCU UCUGCCG | 2.57 ± 0.3 | 0.7 | 22.9 | 6.1 | 26.6 | | |
| 30-28 | UGCCUUUAGCUUAGA | CCUGUCU UCUGCCG | 0.78 ± .07 | 0.4 ± 0.2 | 17.9 | 8.4 | 46.9 | | >130 |
| 30-29 | UGUCUUUAGCUUAGG | UGAUUCCU UCUGCCG | | | | | | | |

TABLE 4-continued

Proposed alignment and observed affinity and bioactivity of TGFβ1 ligands. The sequences of the fixed region (Table 1) are not shown.

| | | Kd1 (nM) | Kd2(pM) | P1 (%) | P2 (%) | P2/P1 (%) | BCG (%) | Ki, nM |
|---|---|---|---|---|---|---|---|---|
| 30-30 | UGUCUUUAGCUUAGG UGAUCCU UCUGCCG | | | | | | | |
| 30-34 | UGUCUAUAGCCUUGA UUACAUCA UCUGCCU | 9.5 ± 1.6 | | 68.5 | | | | |
| 30-35 | UGUCUUUAGCCUAGG UGAUCCU UCUGCCG | 20.7 ± 13.8 | 224 ± 123 | 90.3 | 8.8 | 9.7 | | |
| 30-36 | UGCCUUUAGCUUAGG CAUUCGCCUUCUGCCG | 3.9 ±10 1.1 | | 46.6 | | | | |
| 30-37 | UGUCUUUGGCCUAGG UGAUCCU UCUGCCG | 2.65 ± 0.7 | | 46.6 | | | | |
| 30-39 | UGUCUUUAGCUUAGG UGAUCCU UCUGCCG | 6.02 ± 1.5 | 32.5 ± 16.2 | 48.5 | 13.3 | 27.4 | | |
| 30-43 | UGUCUUUAGCCUAGG UGAUCCU UCUGCCG | 50.5 | | 100 | | | | |
| 30-44 | UGCCUUUAGCUUAGG CAUUGC CUUGCCG | | | | | | | |
| 40-04 | AUGCCUUUGCCUUCAGGUGU AAUUCCUUGAUC UGUCCG | 5.0 ± 0.6 | 1.4 ± 1.2 | 56.7 | 4.2 | 7.4 | | |
| 40-11 | UGCCUUUAGUC UGAAUCUUCUACCA UGAUUC UCUGCCG | 4.6 ± 0.7 | 4.9 ± 3.1 | 68.9 | 8.0 | 11.6 | | |
| 40-39 | UGCCUUUAGCC UAAGUUG AUCUAUUCAGCUU UCUGCCG | 11.5 ± 2.0 | 8.78 ± 6.4 | 64.2 | 3.6 | 5.6 | | |
| 40-41 | UGCCUUUAGCC UGAGUAU ACUGAUGUAUAUUC UCUGCCG | 3.8 ± 0.9 | 1.4 ± 1.1 | 30.8 | 11.1 | 36.0 | | >130 |
| 40-51 | UGCCUUUAGUC UGAAUCUU ACCAUGCGAUUU UCUGCCG | | | | | | | |
| Class 5 | | | | | | | | |
| 20-26 | UCAUCUCUGGGAGUUAAGAUCAUUUGGCCG | | | | | | | |
| 30-04 | UUAACCGUAAAGACGGCAUGAUGUAGUCCG | 5.03 ± 0.8 | | 33.2 | | | | |
| 30-15 | UUGACCGUUAAAGACGGCAUGAUGUGGUCCG | 55.3 | | 95.1 | | | | |
| 30-19 | UUAACCNUAAAUACGGCUUGANUUCUUCCG | 5.7 ± 1.9 | 346 | 28.8 | 13.6 | 47.2 | | 53–522 |
| 30-22 | UUAACCGUAAAGACGGCAUGAUGUUUUCCG | 2.47 | | 32.2 | | | | |
| 30-47 | UUAACCGUAAAGACAGCAUGAUGUAGUCUG | | | | | | | |
| 30-49 | UUAACCGUAAAGACGGCAUGAUGUUGUCCG | | | | | | | |
| Class 6 | | | | | | | | |
| 20-19 | CAAAAUUUUUGGUCAAGCCGUCAUUGCCGC | | | | | | | |
| 20-23 | AA UUUUUGUGAAGACGUU UGCCCGCUUUGCC | | | | | | | |

TABLE 4-continued

Proposed alignment and observed affinity and bioactivity of TGFβ1 ligans. The sequences of the fixed region (Table 1) are not shown.

| | | Kd1 (nM) | Kd2 (pM) | P1 (%) | P2 (%) | P2/P1 (%) | BCG (%) | Ki, nM |
|---|---|---|---|---|---|---|---|---|
| 20-25 | GGAAUUUUGGUAAAGCCG UA UGCCUCGC | | | | | | | |
| 30-08 | CGGAAUUUUU GUUGAGCCG UA UGCCGC | 10.2 ± 2.9 | | 33.8 | | | | |
| 30-32 | GGAAUUUUUGGUAAAGCCG UA UGCCUCGC | | | | | | | |
| 30-50 | GGAAUUUUUGGUAAAGCCG UA UGCCUCGC | | | | | | | |
| Class 7 | | | | | | | | |
| 20-07 | UUGGCAUUGAAAGAGCUGGCAUACAUUCGC | | | | | | | |
| 30-35 | UUGGCAUUGAAAGAGGCGUCAUAUGUUCGC | 23 ± 6.4 | 1.14 ± .6 | 79 | 2.7 | 3.4 | | |
| 30-33 | UGGCAUUGAAAGAGAUCCGAUACCUUCGC | | | | | | | |
| Class 8 | | | | | | | | |
| 20-48 | GAUGAACCGAACCGAGGUUAAGGUGCCAGAGUAGACGCUCAU | | | | | | | |
| 30-31 | ACCGGUAAGGGCACUGCAGGAACACAAUCCCCUAUGCGAC | 100 | | | | | | |
| 40-38 | AGAUAAUUAUCAGCGGUGACGGGGUGCCGGUACUGCCCC | 21.8 ± 5.3 | | 92.7 | | | | |
| Class 9 | | | | | | | | |
| 20-01 | GUCUAUUUUU GCCUCCUCCC | | | | | | | |
| 20-02 | AAUCCUUUCUUAAA CCUCCC | 0.6 | | 5 | | | 0.6 | |
| 20-06 | UGAGUCUUGUUUUU CGUC | 0.3 | | 5 | | | 0.5 | |
| 20-08 | UCCUUUCUAACAUU CCUCCC | | | | | | | |
| 20-09 | GUCGUUGUUUUU CUCCUCCC | | | | | | | |
| 20-10 | UGAGUCUUUCUUU CGUCCC | | | | | | | |
| 20-11 | GUCGUUUUUU GGUCCC | | | | | | | |
| 20-12 | GUUUUUAUUAUUCGUUUGGC | | | | | | | |
| 20-14 | GUCGAUCAUUUUU AGCCUCCC | | | | | | | |
| 20-17 | UGAGUUGAUCUUU CGUCCC | | | | | | | |
| 20-21 | GUCGUUCUUUUUU CCCUCCC | | | | | | | |

TABLE 4-continued

Proposed alignment and observed affinity and bioactivity of TGFβ1 ligans. The sequences of the fixed region (Table 1) are not shown.

| | | Kd1 (nM) | Kd2(pM) | P1 (%) | P2 (%) | P2/P1 (%) | BCG (%) | Ki, nM |
|---|---|---|---|---|---|---|---|---|
| 20-24 | CGCAUCUUCUGUUUCU CCC | | | | | | | |
| 20-27 | GCAGCCUCUGAUUUCU CCC | | | | | | | |
| 20-28 | GUCGUGAUUUU CGUUCUGCC | | | | | | | |
| 20-29 | GUCGUAUUUUU CCGCCUCCC | | | | | | | |
| 20-31 | UCCUCAGCCUCCACUUAUUAUCCUCCC | | | | | | | |
| 20-34 | GUCACUUGUUU ACCUCCC | | | | | | | |
| 20-35 | CGAUUUUUCGUCUUUG GC | | | | | | | |
| 20-37 | CGAUCCUCUUUUC ACUCCC | | | | | | | |
| 20-38 | UCCCAUUUU CUCCUCUCCC | | | | | | | |
| 20-40 | GUUAAUUUUGUCCUCUGGC | | | | | | | |
| 20-41 | UUUUUUCUUUUUUCUUUUUUUU CCG | | | | | | | |
| 20-42 | UCGUCUUUGUUUU CUCCC | | | | | | | |
| 20-47 | UUUUAUUUUCUU CGUCUGGC | | | | | | | |
| 20-49 | UCGUCUAUUUUUU CCCUCCC | | | | | | | |
| 20-50 | CUUUCGUCGUUUU CCUGCC | | | | | | | |
| 30-02 | CCUUGUUUUCUUUUUUCUUUUUUUCACCCC | 5.3 ± 2.8 | 0.8 ± 0.9 | 27.1 | 12.14 | 4.6 | 22.0 | >1300 |
| 30-26 | CCUUUCUUUCUUUUAUUUUCUU CCCCUCCC | | | | | | | |
| 30-45 | GGUCUUUUAUUUUUGUUUUUCU CUGUGCCC | | | | | | | |
| 30-48 | UUUUUUCUUUUCCUUCCCUUUUCUUACCG | | | | | | | |
| 40-15 | CUCUAACUUCUUUUCGCCUGUGUUUUCUUUUU GCUG | | | | | | | 31.6 | |
| 40-17 | GGUCGUUUUGUUUUGUUUUUUGUAGCCCGGUCAUCCC | | | | | | | 35.13 | |
| 40-25 | UGUCGAUCGUUUGCUGUUUGAUUUCUUUU GUCCCUCCCGUG | | | | | | | 51.9 | |
| 40-37 | CUCCUAUAUUCAUGUAUGUUUUUUUCUU CCAGCUUGCCC | | | | | | | 29.6 | |
| 40-43 | AUCCUUUUUUAGCUUUUUCUUUUU CCUGCCCCACUUCCC | 2.2 ± 1.7 | | 12 | | | 13.2 | |

TABLE 4-continued

Proposed alignment and observed affinity and bioactivity of TGFβ1 ligans. The sequences of the fixed region (Table 1) are not shown.

| | | Kd1 (nM) | Kd2(pM) | P1 (%) | P2 (%) | P2/P1 (%) | BCG (%) | Ki, nM |
|---|---|---|---|---|---|---|---|---|
| 40-45 | GGGCUUUCCUUUAGUACUUUUUGUUU | CGCUCCCCCC | | | | | 10.7 | |
| 40-57 | GGUGUCGUCUUUC | AACCCCU | | | | | | |
| 40-70 | GGAUGGUCAGUUUCGGUUUUU | CAUAUGUUUAUUUUCCCCC | | | | | | |
| 40-71 | UAUUGACUUUUGUUUCUUUUUCUUUGCCUGGUCCC | | | | | | | |
| 40-73 | CUUCUUUUUCUCUUUUUCUUUAUGUCUUCUU | CAUGCCG | | | | | | |

Kd1 = Dissociation rate constant in nanomolar of the low affinity component of biphasic binding curves or dissociation rate constant in nanomolar of monophasic binding curves
Kd2 = Dissociation rate constant in picomolar of the high affinity component of biphasic binding curves
P1 = Plateau values in % of monophasic curves or of the low affinity component of biphasic curves
P2 = Plateau values in % of the high affinity component of biphasic curves
P2/P1 = Fraction in % of the high affinity component of hiphasic curves
Ki = Inhibition constant in nanomolar obtained from the MLEC assay
BCG = Nitrocellulose binding background expressed as % of input

TABLE 5

Binding Specificity of TGFβ1 Ligands 40-03 and 40-60

| Target | $K_D$Target/$K_D$hTGFβ1 40-03 | $K_D$Target/$K_D$hTGFβ1 40-60 |
|---|---|---|
| hTGFβ1 | 1 | 1 |
| hTGFβ2 | >340,000 | >340,000 |
| hKGF | >34,000 | >34,000 |
| hVEGF | >340,000 | >340,000 |

When applicable, the high affinity component of biphasic binding was used

TABLE 6

Results of TGFβ1 SELEX with random regions of 20 30 and 40N expressed by the distribution of ligands in the different classes and the binding and inhibitory activity of these classes

| | SELEX Pools | | | Affinities | | |
|---|---|---|---|---|---|---|
| | 40N | 30N | 20N | Biph[1]. | $K_D$~pM[2] | $K_i$[3] |
| Total clones | 64 | 48 | 40 | | | |
| Unique clones | 61 | 37 | 40 | | | |
| Class 1 | 39.3% | | | + | + | +++ |
| Class 2 | 26.2% | | | − | − | − |
| Class 3 | 8.2% | | | + | + | ++ |
| Class 4 | 8.2% | 56.7% | 20.0%[4] | + | + | ± |
| Class 5 | | 16.2% | 2.5%[4] | + | + | + |
| Class 6 | | 8.1% | 7.5%[4] | − | − | ND |
| Class 7 | | 5.4% | 2.5%[4] | ± | − | ND |
| Class 8 | 1.6% | 2.7% | 2.5%[4] | − | − | ND |
| Class 9 | 16.4% | 10.8% | 65.0% | | NC[5] | − |
| Length of 40 | 59 (96.7%) | 1 (2.7%) | 1 (2.5%) | | | |
| Length of 30 | 1 (1.6%) | 36 (97.3%) | 15 (37.5%) | | | |
| Length of 20 | 1 (1.6%) | | 24 (60.0%) | | | |

[1]Biphasic binding is shown by plus (+), monophasic by minus (−), and unclear results by plus/minus (±)
[2]Low pmolar $K_D$ values are shown by plus (+) and $K_D$ values similar to random RNA are shown by minus (−)
[3]High, intermediate, low, and possible bioactivity is shown by 3 pluses (+++), two pluses (++), one plus (+) or plus/minus (±), respectively
[4]longer than 20N
[5]nitrocellulose binders

We claim:

1. A purified and isolated non-naturally occurring RNA ligand to TGFβ1 wherein said ligand is selected from the group consisting of the sequences set forth in Table 3 (SEQ ID NOS: 6–143).

* * * * *

SEQUENCE LISTING (1) GENERAL INFORMATION:

(iii) NUMBER OF SEQUENCES: 143

(2) INFORMATION FOR SEQ ID NO: 1:

(i) SEQUENCE CHARACTERISTICS:
      (A) LENGTH: 71 base pairs
      (B) TYPE: nucleic acid
      (C) STRANDEDNESS: single
      (D) TOPOLOGY: linear (ii) MOLECULE TYPE: DNA (ix) FEATURE:
      (D) OTHER INFORMATION: All pyrimidines are 2'-F modified (xi) SEQUENCE DESCRIPTION: SEQ ID NO: 1:

GGGAGGACGA TGCGGNNNNN NNNNNNNNNN NNNNNNNNNN NNNNNNNNNN　　　　50

```
NNNNNCAGAC GACTCGCCCG A                                          71

(2) INFORMATION FOR SEQ ID NO: 2:

(i) SEQUENCE CHARACTERISTICS:
        (A) LENGTH:  61 base pairs
        (B) TYPE:  nucleic acid
        (C) STRANDEDNESS:  single
        (D) TOPOLOGY:  linear (ii) MOLECULE TYPE:  DNA (ix) FEATURE:
        (D) OTHER INFORMATION:  All pyrimidines are 2'-F modified (xi) SEQUENCE DESCRIPTION:  SEQ ID NO: 2:

GGGAGGACGA TGCGGNNNNN NNNNNNNNNN NNNNNNNNNN NNNNNCAGAC            50

GACTCGCCCG A                                                      61

(2) INFORMATION FOR SEQ ID NO: 3:

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  DNA (ix) FEATURE:
        (D) OTHER INFORMATION:  All pyrimidines are 2'-F modified (xi) SEQUENCE DESCRIPTION:  SEQ ID NO: 3:

GGGAGGACGA TGCGGNNNNN NNNNNNNNNN NNNNNCAGAC GACTCGCCCG            50

A                                                                 51

(2) INFORMATION FOR SEQ ID NO: 4:

(i) SEQUENCE CHARACTERISTICS:
        (A) LENGTH:  32 base pairs
        (B) TYPE:  nucleic acid
        (C) STRANDEDNESS:  single
        (D) TOPOLOGY:  linear (ii) MOLECULE TYPE:  DNA (ix) FEATURE:
        (D) OTHER INFORMATION:  All pyrimidines are 2'-F modified (xi) SEQUENCE DESCRIPTION:  SEQ ID NO: 4:

TAATACGACT CACTATAGGG AGGACGATGC GG                               32

(2) INFORMATION FOR SEQ ID NO: 5:

(i) SEQUENCE CHARACTERISTICS:
        (A) LENGTH:  16 base pairs
        (B) TYPE:  nucleic acid
        (C) STRANDEDNESS:  single
        (D) TOPOLOGY:  linear (ii) MOLECULE TYPE:  DNA (ix) FEATURE:
        (D) OTHER INFORMATION:  All pyrimidines are 2'-F modified (xi) SEQUENCE DESCRIPTION:  SEQ ID NO: 5:

TCGGGCGAGT CGTCTG                                                 16
```

```
(2) INFORMATION FOR SEQ ID NO: 6:

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 6:

GGGAGGACGA UGCGGGUCUA UUUUUGCCUC CUCCCCAGAC GACUCGCCCG          50

A                                                               51

(2) INFORMATION FOR SEQ ID NO: 7:

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 7:

GGGAGGACGA UGCGGAAUCC UUUCUUAAAC CUCCCCAGAC GACUCGCCCG          50

A                                                               51

(2) INFORMATION FOR SEQ ID NO: 8:

(i) SEQUENCE CHARACTERISTICS:
        (A) LENGTH:  61 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 8:

GGGAGGACGA UGCGGUGUCU UUAGCUUAGG UUAUUCCUUC UGCCGCAGAC          50

GACUCGCCCG A                                                    61

(2) INFORMATION FOR SEQ ID NO: 9:

(i) SEQUENCE CHARACTERISTICS:
        (A) LENGTH:  61 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 9:

GGGAGGACGA UGCGGUGUCU UUAGCUUAGG UGAUUCCUUC UGCCGCAGAC          50

GACUCGCCCG A                                                    61
```

(2) INFORMATION FOR SEQ ID NO: 10:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 10:

```
GGGAGGACGA UGCGGUGUCU CUACCUUAGG UUGAUUCCUU CUACCGCAGA          50

CGACUCGCCC GA                                                   62
```

(2) INFORMATION FOR SEQ ID NO: 11:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 11:

```
GGGAGGACGA UGCGGUGAGU CUUGUUUUUU CGUCCAGACG ACUCGCCCGA          50
```

(2) INFORMATION FOR SEQ ID NO: 12:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 12:

```
GGGAGGACGA UGCGGUUGGC AUUGAAAGAG CUGGCAUACA UUCGCCAGAC          50

GACUCGCCCG A                                                    61
```

(2) INFORMATION FOR SEQ ID NO: 13:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 13:

```
GGGAGGACGA UGCGGUCCUU UCUAACAUUC CUCCCCAGAC GACUCGCCCG          50

A                                                               51
```

(2) INFORMATION FOR SEQ ID NO: 14:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 14:

```
GGGAGGACGA UGCGGGUCGU UGUUUUCUC CUCCCCAGAC GACUCGCCCG          50
A                                                              51
```

(2) INFORMATION FOR SEQ ID NO: 15:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 15:

```
GGGAGGACGA UGCGGUGAGU CUUUCUUUUC GUCCCCAGAC GACUCGCCCG          50
A                                                              51
```

(2) INFORMATION FOR SEQ ID NO: 16:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 16:

```
GGGAGGACGA UGCGGGUCGU UUUUUGGUC CUCCAGACGA CUCGCCCGA           49
```

(2) INFORMATION FOR SEQ ID NO: 17:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 17:

```
GGGAGGACGA UGCGGGUUUU UAUUAUUCGU UUGGCCAGAC GACUCGCCCG          50
A                                                              51
```

(2) INFORMATION FOR SEQ ID NO: 18:

```
        (i) SEQUENCE CHARACTERISTICS:
             (A) LENGTH:  52 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F modified (xi) SEQUENCE DESCRIPTION:  SEQ ID NO: 18:

GGGAGGACGA UGCGGGUCGA UCAUUUUUAG CCUCCCCAGA CGACUCGCCCC          50

GA                                                              52

(2) INFORMATION FOR SEQ ID NO: 19:

(i) SEQUENCE CHARACTERISTICS:
             (A) LENGTH:  51 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F modified (xi) SEQUENCE DESCRIPTION:  SEQ ID NO: 19:

GGGAGGACGA UGCGGUGAGU UGAUCUUUUC GUCCCCAGAC GACUCGCCCG          50

A                                                               51

(2) INFORMATION FOR SEQ ID NO: 20:

(i) SEQUENCE CHARACTERISTICS:
             (A) LENGTH:  60 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F modified (xi) SEQUENCE DESCRIPTION:  SEQ ID NO: 20:

GGGAGGACGA UGCGGUGCCU UUAGCUUAGG CAUUGCCUUC UGUGCAGACG          50

ACUCGCCCGA                                                      60

(2) INFORMATION FOR SEQ ID NO: 21:

(i) SEQUENCE CHARACTERISTICS:
             (A) LENGTH:  61 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F modified (xi) SEQUENCE DESCRIPTION:  SEQ ID NO: 21:

GGGAGGACGA UGCGGCAAAA UUUUUGGUCA AGCCGUCAUU GCCGCCAGAC          50

GACUCGCCCG A                                                    61
```

(2) INFORMATION FOR SEQ ID NO: 22:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 22:

```
GGGAGGACGA UGCGGGUCGU UCUUUUUUCC CUCCCCAGAC GACUCGCCCG      50
A                                                          51
```

(2) INFORMATION FOR SEQ ID NO: 23:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 23:

```
GGGAGGACGA UGCGGAAUUU UUGUGAAGAC GUUUGCCGCU UUGCCCAGAC      50
GACUCGCCCG A                                               61
```

(2) INFORMATION FOR SEQ ID NO: 24:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 24:

```
GGGAGGACGA UGCGGCGCAU CUUCUGUUUU CUCCCCAGAC GACUCGCCCG      50
A                                                          51
```

(2) INFORMATION FOR SEQ ID NO: 25:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 25:

```
GGGAGGACGA UGCGGGGAAU UUUUGGUAAA GCCGUAUGCC UCGCCAGACG      50
ACUCGCCCGA                                                 60
```

(2) INFORMATION FOR SEQ ID NO: 26:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 26:

```
GGGAGGACGA UGCGGUCAUC UCUGGGAGUU AAGAUCAUUU GGCCGCAGAC        50

GACUCGCCCG A                                                  61
```

(2) INFORMATION FOR SEQ ID NO: 27:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 27:

```
GGGAGGACGA UGCGGGCAGC CUCUGAUUUU CUCCCCAGAC GACUCGCCCG        50

A                                                             51
```

(2) INFORMATION FOR SEQ ID NO: 28:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 28:

```
GGGAGGACGA UGCGGGUCGU GAUUUUCGUU CUGCCCAGAC GACUCGCCCG        50

A                                                             51
```

(2) INFORMATION FOR SEQ ID NO: 29:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 29:

```
GGGAGGACGA UGCGGGUCGU AUUUUUUCCG CCUCCCCAGA CGACUCGCCC        50

GA                                                            52
```

(2) INFORMATION FOR SEQ ID NO: 30:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 30:

```
GGGAGGACGA UGCGGUCCUC AGCCUCUCAC UUAUUAUCCU CCCCAGACGA          50

CUCGCCCGA                                                       59
```

(2) INFORMATION FOR SEQ ID NO: 31:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 31:

```
GGGAGGACGA UGCGGGUCUA CUUGUUUUAC CUCCCCAGAC GACUCGCCCG          50

A                                                               51
```

(2) INFORMATION FOR SEQ ID NO: 32:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 32:

```
GGGAGGACGA UGCGGCGAUU UUUUCGUCUU UUGGCCAGAC GACUCGCCCG          50

A                                                               51
```

(2) INFORMATION FOR SEQ ID NO: 33:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 33:

```
GGGAGGACGA UGCGGUGUCU AUAGCCUUGA UUAUAUCAUC UGCCGCAGAC          50
```

GACUCGCCCG A61

(2) INFORMATION FOR SEQ ID NO: 34:

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 34:

GGGAGGACGA UGCGGCGAUU CCUCUUUUCA CUCCCCAGAC GACUCGCCCG          50

A                                                              51

(2) INFORMATION FOR SEQ ID NO: 35:

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 35:

GGGAGGACGA UGCGGUCCCA UUUUUCUCCU CUCCCCAGAC GACUCGCCCG          50

A                                                              51

(2) INFORMATION FOR SEQ ID NO: 36:

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 36:

GGGAGGACGA UGCGGGUUAA UUUUUGUCCU CUGGCCAGAC GACUCGCCCG          50

A                                                              51

(2) INFORMATION FOR SEQ ID NO: 37:

(i) SEQUENCE CHARACTERISTICS:
        (A) LENGTH:  56 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION: SEQ ID NO: 37:

GGGAGGACGA UGCGGUUUUU UUCUUUUUUC UUUUUUUCCG CAGACGACUC        50

GCCCGA                                                        56

(2) INFORMATION FOR SEQ ID NO: 38:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-F modified (xi) SEQUENCE DESCRIPTION: SEQ ID NO: 38:

GGGAGGACGA UGCGGUCGUC UUUGUUUUUC UCCCCAGACG ACUCGCCCGA        50

(2) INFORMATION FOR SEQ ID NO: 39:

(i) SEQUENCE CHARACTERISTICS:
       (A) LENGTH: 61 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-F modified (xi) SEQUENCE DESCRIPTION: SEQ ID NO: 39:

GGGAGGACGA UGCGGUGUCU AUAGCCUUGA UUACAUCAUC UGCCGCAGAC        50

GACUCGCCCG A                                                  61

(2) INFORMATION FOR SEQ ID NO: 40:

(i) SEQUENCE CHARACTERISTICS:
       (A) LENGTH: 61 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-F modified (xi) SEQUENCE DESCRIPTION: SEQ ID NO: 40:

GGGAGGACGA UGCGGUGCCU UUAGCUUAGG CAUUGCCUUC UGCCGCAGAC        50

GACUCGCCCG A                                                  61

(2) INFORMATION FOR SEQ ID NO: 41:

(i) SEQUENCE CHARACTERISTICS:
       (A) LENGTH: 61 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All pyrimidines are 2'-F modified (xi) SEQUENCE DESCRIPTION: SEQ ID NO: 41:

```
GGGAGGACGA UGCGGUGUCU AUAGCUUGAU UUUUAAUUUC UGCCGCAGAC        50

GACUCGCCCG A                                                  61

(2) INFORMATION FOR SEQ ID NO:42 :

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 42:

GGGAGGACGA UGCGGUUUUA UUUUCUUCGU CUGGCCAGAC GACUCGCCCG        50

A                                                             51

(2) INFORMATION FOR SEQ ID NO: 43:

(i) SEQUENCE CHARACTERISTICS:
        (A) LENGTH:  73 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 43:

GGGAGGACGA UGCGGGAUGA ACCGAACCGA GGUUAAGGUG CCAGAGUAGA        50

CGCUCAUCAG ACGACUCGCC CGA                                     73

(2) INFORMATION FOR SEQ ID NO: 44:

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 44:

GGGAGGACGA UGCGGUCGUC UAUUUUUUCC CUCCCCAGAC GACUCGCCCG        50

A                                                             51

(2) INFORMATION FOR SEQ ID NO: 45:

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified
```

(xi) SEQUENCE DESCRIPTION: SEQ ID NO: 45:

GGGAGGACGA UGCGGCUUUC GUCUGUUUUC CUGCCCAGAC GACUCGCCCG          50

A                                                              51

(2) INFORMATION FOR SEQ ID NO: 46:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 46:

GGGAGGACGA UGCGGUGUCU UUAGCCUAGG UGAUUCCUUC UGCCGCAGAC          50

GACUCGCCCG A                                                   61

(2) INFORMATION FOR SEQ ID NO: 47:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 47:

GGGAGGACGA UGCGGCCUUG UUUUCUUUUU UCUUUUUUCA CCCCCAGACG          50

ACUCGCCCGA                                                     60

(2) INFORMATION FOR SEQ ID NO: 48:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 48:

GGGAGGACGA UGCGGUGUCU UUAGCCCAGG UGAUUCCUUC UGCCGCAGAC          50

GACUCGCCCG A                                                   61

(2) INFORMATION FOR SEQ ID NO: 49:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 49:

GGAGGACGA UGCGGUUAAC CGUAAAGACG GCAUGAUGUA GUCCGCAGAC          50

GACUCGCCCG A                                                   61

(2) INFORMATION FOR SEQ ID NO: 50:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 50:

GGGAGGACGA UGCGGUUUUU UUAGCUUAGG UGAUUCCUUC NNCCUCAGAC          50

GACUCGCCCG A                                                   61

(2) INFORMATION FOR SEQ ID NO: 51:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 51:

GGGAGGACGA UGCGGUGCCU UUAGCUUAGG CUUUGCCUUC UGCCGCAGAC          50

GACUCGCCCG A                                                   61

(2) INFORMATION FOR SEQ ID NO: 52:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 52:

GGGAGGACGA UGCGGCGGAA UUUUUGUUGA GCCGUAUGCC GCCAGACGAC          50

UCGCCCGA                                                       58

(2) INFORMATION FOR SEQ ID NO: 53:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:

(D) OTHER INFORMATION: All pyrimidines are 2'-F modified (xi) SEQUENCE DESCRIPTION: SEQ ID NO: 53:

GGGAGGACGA UGCGGUGCCU UUAGCUUAGG UGAUUCCUUC UGCCGCAGAC    50

GACUCGCCCG A    61

(2) INFORMATION FOR SEQ ID NO: 54:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 54:

GGGAGGACGA UGCGGUGUCU UUAGCCUAGG UGAUUCCUUC UGCCGCAGAC    50

GACUCGCCCG A    61

(2) INFORMATION FOR SEQ ID NO: 55:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 55:

GGGAGGACGA UGCGGUGUCU AUAGCCUGAU UUUUAAUCUC UGCCGCAGAC    50

GACUCGCCCG A    61

(2) INFORMATION FOR SEQ ID NO: 56:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 56:

GGGAGGACGA UGCGGUUGAC CGUUAAGACG GCAUGAUGUG GUCCGCAGAC    50

GACUCGCCCG A    61

(2) INFORMATION FOR SEQ ID NO: 57:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
    (D) OTHER INFORMATION: All pyrimidines are 2'-F modified (xi) SEQUENCE DESCRIPTION: SEQ ID NO: 57:

GGGAGGACGA UGCGGUGCCU UUAGCUUAGG CAUUGCCUUC UGCCGCAGAC    50

GACUCGCCCG A    61

(2) INFORMATION FOR SEQ ID NO: 58:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All pyrimidines are 2'-F modified (xi) SEQUENCE DESCRIPTION: SEQ ID NO: 58:

GGGAGGACGA UGCGGUGCCU UUAGCUUAGG CUUUGCCUUC UGCCGCAGAC    50

GACUCGCCCG A    61

(2) INFORMATION FOR SEQ ID NO: 59:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All pyrimidines are 2'-F modified (xi) SEQUENCE DESCRIPTION: SEQ ID NO: 59:

GGGAGGACGA UGCGGUUAAC CNUAAAUACG GCUUGANUUC UUCCGCAGAC    50

GACUCGCCCG A    61

(2) INFORMATION FOR SEQ ID NO: 60:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All pyrimidines are 2'-F modified (xi) SEQUENCE DESCRIPTION: SEQ ID NO: 60:

GGGAGGACGA UGCGGUGCCU UUAGCUUAGG CAUUGCCUUC UGCCGCAGAC    50

GACUCGCCCG A    61

(2) INFORMATION FOR SEQ ID NO: 61:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 61:

GGGAGGACGA UGCGGUUAAC CGUAAAGACG GCAUGAUGUU UUCCGCAGAC          50

GACUCGCCCG A                                                    61

(2) INFORMATION FOR SEQ ID NO: 62:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 62:

GGGAGGACGA UGCGGUUGGC AUUGAAAGAG GCGUCAUAUG UUCGCCAGAC          50

GACUCGCCCG A                                                    61

(2) INFORMATION FOR SEQ ID NO: 63:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 63:

GGGAGGACGA UGCGGCCUUU CUUUCUUUUU AUUUUCUUCC CCUCCCCAGA          50

CGACUCGCCC GA                                                   62

(2) INFORMATION FOR SEQ ID NO: 64:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 64:

GGGAGGACGA UGCGGUGCCU UUAGCCUAGA CCUUGUCUUC UGCCGCAGAC          50

GACUCGCCCG A                                                    61

(2) INFORMATION FOR SEQ ID NO: 65:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 65:

GGGAGGACGA UGCGGUGUCU UUAGCCUAGG UGAUUCCUUC UGCCGCAGAC         50

GACUCGCCCG A                                                  61

(2) INFORMATION FOR SEQ ID NO: 66:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 66:

GGGAGGACGA UGCGGUGUCU UUAGCCUAGG UGAUUCCUUC UGCCGCAGAC         50

GACUCGCCCG A                                                  61

(2) INFORMATION FOR SEQ ID NO: 67:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 67:

GGGAGGACGA UGCGGACCGG UAAGGGCACU GCAGGAACAC AAUCCCCUAU         50

GCGACCAGAC GACUCGCCCG A                                       71

(2) INFORMATION FOR SEQ ID NO:68 :

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 68:

GGGAGGACGA UGCGGGGAAU UUUUGGUAAA GCCGUAUGCC UCGCCAGACG         50

ACUCGCCCGA                                                    60

(2) INFORMATION FOR SEQ ID NO: 69:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 69:

GGGAGGACGA UGCGGUGGCA UUGAAAGAGA UCGCAUACCU UCGCCAGACG         50

ACUCGCCCGA                                                    60

(2) INFORMATION FOR SEQ ID NO: 70:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 70:

GGGAGGACGA UGCGGUGUCU AUAGCCUUGA UUACAUCAUC UGCCUCAGAC         50

GACUCGCCCG A                                                  61

(2) INFORMATION FOR SEQ ID NO: 71:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 71:

GGGAGGACGA UGCGGUGUCU UUAGCCUAGG UGAUUCCUUC UGCCUCAGAC         50

GACUCGCCCG A                                                  61

(2) INFORMATION FOR SEQ ID NO: 72:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-F modified (xi) SEQUENCE DESCRIPTION: SEQ ID NO: 72:

GGGAGGACGA UGCGGUGCCU UUAGCUUAUG CAUUGCCUUC UGCCGCAGAC         50

GACUCGCCCG A                                                  61

(2) INFORMATION FOR SEQ ID NO: 73:

(i) SEQUENCE CHARACTERISTICS:
            (A) LENGTH: 62 base pairs
            (B) TYPE: nucleic acid
            (C) STRANDEDNESS: single
            (D) TOPOLOGY: linear

```
        (ii) MOLECULE TYPE:  RNA (ix) FEATURE:
             (D) OTHER INFORMATION:  All pyrimidines are 2'-F modified (xi) SEQUENCE DESCRIPTION:  SEQ ID NO: 73:

GGGAGGACGA UGCGGUGCCU UUAGCUUAGG CAUUCGCCUU CUGCCGCAGA         50

CGACUCGCCC GA                                                 62

(2) INFORMATION FOR SEQ ID NO: 74:

(i) SEQUENCE CHARACTERISTICS:
             (A) LENGTH:  61 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F modified (xi) SEQUENCE DESCRIPTION:  SEQ ID NO: 74:

GGGAGGACGA UGCGGUGUCU UUGGCCUAGG UGAUUCCUUC UGCCGCAGAC         50

GACUCGCCCG A                                                  61

(2) INFORMATION FOR SEQ ID NO: 75:

(i) SEQUENCE CHARACTERISTICS:
             (A) LENGTH:  61 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F modified (xi) SEQUENCE DESCRIPTION:  SEQ ID NO: 75:

GGGAGGACGA UGCGGUGUCU UUAGCUUAGG UGAUUCCUUC UGCCGCAGAC         50

GACUCGCCCG A                                                  61

(2) INFORMATION FOR SEQ ID NO: 76:

(i) SEQUENCE CHARACTERISTICS:
             (A) LENGTH:  61 base pairs
             (B) TYPE:  nucleic acid
             (C) STRANDEDNESS:  single
             (D) TOPOLOGY:  linear (ii) MOLECULE TYPE:  RNA (ix) FEATURE:
             (D) OTHER INFORMATION:  All pyrimidines are 2'-F modified (xi) SEQUENCE DESCRIPTION:  SEQ ID NO: 76:

GGGAGGACGA UGCGGUGUCU UUAGCCUAGG UGAUUCCUUC UGCCGCAGAC         50

GACUCGCCCG A                                                  61

(2) INFORMATION FOR SEQ ID NO: 77:

(i) SEQUENCE CHARACTERISTICS:
             (A) LENGTH:  59 base pairs
             (B) TYPE:  nucleic acid
             (C) STRANDEDNESS:  single
```

(D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 77:

GGGAGGACGA UGCGGUGCCU UUAGCUUAGG CAUUGCCUUG CCGCAGACGA          50

CUCGCCCGA                                                      59

(2) INFORMATION FOR SEQ ID NO: 78:

(i) SEQUENCE CHARACTERISTICS:
        (A) LENGTH:  62 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 78:

GGGAGGACGA UGCGGGGUCU UUUAUUUUUU GUUUUUCUCU GUGCCCCAGA          50

CGACUCGCCC GA                                                  62

(2) INFORMATION FOR SEQ ID NO: 79:

(i) SEQUENCE CHARACTERISTICS:
        (A) LENGTH:  61 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 79:

GGGAGGACGA UGCGGUUAAC CGUAAAGACA GCAUGAUGUA GUCUGCAGAC          50

GACUCGCCCG A                                                   61

(2) INFORMATION FOR SEQ ID NO: 80:

(i) SEQUENCE CHARACTERISTICS:
        (A) LENGTH:  60 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 80:

GGGAGGACGA UGCGGUUUUU UUCUUUUCCU UCCUUUUCUU ACCGCAGACG          50

ACUCGCCCGA                                                     60

(2) INFORMATION FOR SEQ ID NO: 81:

(i) SEQUENCE CHARACTERISTICS:
        (A) LENGTH:  61 base pairs
        (B) TYPE:  nucleic acid

```
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F modified (xi) SEQUENCE DESCRIPTION:  SEQ ID NO: 81:

GGGAGGACGA UGCGGUUAAC CGUAAAGACG GCAUGAUGUU GUCCGCAGAC         50

GACUCGCCCG A                                                  61

(2) INFORMATION FOR SEQ ID NO: 82:

(i) SEQUENCE CHARACTERISTICS:
            (A) LENGTH:  60 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F modified (xi) SEQUENCE DESCRIPTION:  SEQ ID NO: 82:

GGGAGGACGA UGCGGGGAAU UUUUGGUAAA GCCGUAUGCC UCGCCAGACG         50

ACUCGCCCGA                                                    60

(2) INFORMATION FOR SEQ ID NO: 83:

(i) SEQUENCE CHARACTERISTICS:
            (A) LENGTH:  72 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F modified (xi) SEQUENCE DESCRIPTION:  SEQ ID NO: 83:

GGGAGGACGA UGCGGGCCAA GGUUACGCCG UCGGACCCUG CUGCCAACAU         50

CCUCCCCAGA CGACUCGCCC GA                                      72

(2) INFORMATION FOR SEQ ID NO: 84:

(i) SEQUENCE CHARACTERISTICS:
            (A) LENGTH:  70 base pairs
            (B) TYPE:  nucleic acid
            (C) STRANDEDNESS:  single
            (D) TOPOLOGY:  linear (ii) MOLECULE TYPE:  RNA (ix) FEATURE:
            (D) OTHER INFORMATION:  All pyrimidines are 2'-F modified (xi) SEQUENCE DESCRIPTION:  SEQ ID NO: 84:

GGGAGGACGA UGCGGGGGUU AUUGGGCGUC AACAUCCCCG AUUCUUUUCA         50

CGUCCAGACG ACUCGCCCGA                                         70

(2) INFORMATION FOR SEQ ID NO: 85:

(i) SEQUENCE CHARACTERISTICS:
            (A) LENGTH:  71 base pairs
```

```
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 85:

GGGAGGACGA UGCGGAUGCC UUUUGCCUUC AGGGUGUAAU UCCUUGAUCU          50

GUCCGCAGAC GACUCGCCCG A                                        71

(2) INFORMATION FOR SEQ ID NO: 86:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 86:

GGGAGGACGA UGCGGAACAA GGUUACGCCG UCGGACCCUG CUGCCAACAU          50

CCUCCCCAGA CGACUCGCCC GA                                       72

(2) INFORMATION FOR SEQ ID NO: 87:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 87:

GGGAGGACGA UGCGGUUAGG GGCGUCAACA CCGCUAUCAU AAUUUUCGCC          50

UUCCCCAGAC GACUCGCCCG A                                        71

(2) INFORMATION FOR SEQ ID NO: 88:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 88:

GGGAGGACGA UGCGGCGCAA GGUUACGCCG UCGGACCCUG CUGCCAACAU          50

CCUCCCAGAC GACUCGCCCG A                                        71

(2) INFORMATION FOR SEQ ID NO: 89:

(i) SEQUENCE CHARACTERISTICS:
```

(A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 89:

GGGAGGACGA UGCGGUGCCU UUAGUCUGAA UCUUCUACCA UGAUUCUCUG            50

CCGCAGACGA CUCGCCCGA                                             69

(2) INFORMATION FOR SEQ ID NO: 90:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 90:

GGGAGGACGA UGCGGGACCC UUGUCUGCGA UUCAACUCGU AGGUUUUCUC            50

ACGUGCAGAC GACUCGCCCG A                                          71

(2) INFORMATION FOR SEQ ID NO: 91:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 91:

GGGAGGACGA UGCGGAGCAA GGUUACGAGG UCGGACCCUG CUGCCAACAU            50

CCUCCCCAGA CGACUCGCCC GA                                         72

(2) INFORMATION FOR SEQ ID NO: 92:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 92:

GGGAGGACGA UGCGGCAUUA UGGCGUCAAC AUGCCGGUUU UCGAUUCUCA            50

UUGUCCAGAC GACUCGCCCG A                                          71

(2) INFORMATION FOR SEQ ID NO: 93:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 93:

GGGAGGACGA UGCGGCUCUA ACUUCUUUUU CGCCUGUGUG UUUUCUUUUU          50

GCUGCAGACG ACUCGCCCGA                                          70

(2) INFORMATION FOR SEQ ID NO: 94:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 94:

GGGAGGACGA UGCGGUUAGG GGCGUCAACA CCGCUAUUAC AUCUUUCGCC          50

UCCCCAGACG ACUCGCCCGA                                          70

(2) INFORMATION FOR SEQ ID NO: 95:

(i) SEQUENCE CHARACTERISTICS:
        (A) LENGTH:  69 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 95:

GGGAGGACGA UGCGGGGUCG UUUUGUUUUU GUUUUUUGUA GCCCGGUCAU          50

CCCCAGACGA CUCGCCCGA                                           69

(2) INFORMATION FOR SEQ ID NO: 96:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 96:

GGGAGGACGA UGCGGUUAGC GCGAGUUCAA CACCGCAUGU GAUUCUUUCG          50

CCUCCCAGAC GACUCGCCCG A                                        71

(2) INFORMATION FOR SEQ ID NO: 97:

```
      (i) SEQUENCE CHARACTERISTICS:
          (A) LENGTH:  72 base pairs
          (B) TYPE:  nucleic acid
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-F modified (xi) SEQUENCE DESCRIPTION:  SEQ ID NO: 97:

GGGAGGACGA UGCGGUACAA GGUUACGCCG UCGGACCCUG CUGCCAACAU            50

CCUCCCCAGA CGACUCGCCC GA                                          72

(2) INFORMATION FOR SEQ ID NO: 98:

(i) SEQUENCE CHARACTERISTICS:
          (A) LENGTH:  70 base pairs
          (B) TYPE:  nucleic acid
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-F modified (xi) SEQUENCE DESCRIPTION:  SEQ ID NO: 98:

GGGAGGACGA UGCGGGACCC UUGUCUGCGA UUCAACUCGU AGGUCUUCUC            50

CGUGCAGACG ACUCGCCCGA                                             70

(2) INFORMATION FOR SEQ ID NO: 99:

(i) SEQUENCE CHARACTERISTICS:
          (A) LENGTH:  69 base pairs
          (B) TYPE:  nucleic acid
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-F modified (xi) SEQUENCE DESCRIPTION:  SEQ ID NO: 99:

GGGAGGACGA UGCGGUUAGG GGCGUCAACA CCGCUAUUAC AAUUUUCGCU            50

UCCCAGACGA CUCGCCCGA                                              69

(2) INFORMATION FOR SEQ ID NO: 100:

(i) SEQUENCE CHARACTERISTICS:
          (A) LENGTH:  69 base pairs
          (B) TYPE:  nucleic acid
          (C) STRANDEDNESS:  single
          (D) TOPOLOGY:  linear (ii) MOLECULE TYPE:  RNA (ix) FEATURE:
          (D) OTHER INFORMATION:  All pyrimidines are 2'-F modified (xi) SEQUENCE DESCRIPTION:  SEQ ID NO: 100:

GGGAGGACGA UGCGGUUAGG GGCGUCAACA CCGCUAUUAC AAUCUUCGCU            50

UCCCAGACGA CUCGCCCGA                                              69
```

(2) INFORMATION FOR SEQ ID NO: 101:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 101:

```
GGGAGGACGA UGCGGUUAUG GGCGUCAACA CCGCUAUUAC AACUUUCGCU      50

UUCCCAGACG ACUCGCCCGA                                       70
```

(2) INFORMATION FOR SEQ ID NO: 102:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 102:

```
GGGAGGACGA UGCGGUGUCG AUCGUUUGCU GUUUGAUUUC UUUUGUCCCU      50

CCCGUGCAGA CGACUCGCCC GA                                    72
```

(2) INFORMATION FOR SEQ ID NO: 103:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 103:

```
GGGAGGACGA UGCGGUUAGG GGCGUCAACA UCGCUAUUAC AAUCUUCGCC      50

UUCCCAGACG ACUCGCCCGA                                       70
```

(2) INFORMATION FOR SEQ ID NO: 104:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 104:

```
GGGAGGACGA UGCGGUUAGG GGCGUCAACA CCGCUAUUAC AACUUUCGCC      50

UCACCAGACG ACUCGCCCGA                                       70
```

(2) INFORMATION FOR SEQ ID NO: 105:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 105:

```
GGGAGGACGA UGCGGGACCC UUUUCUGCGA UUCAACUCGU ACGUCUUCUC        50

ACGUGCAGAC GACUCGCCCG A                                      71
```

(2) INFORMATION FOR SEQ ID NO: 106:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 106:

```
GGGAGGACGA UGCGGUUAAG GGCGUCAACA CCGCUAUUAA ACUUUCGCUU        50

CCCAGACGAC UCGCCCGA                                          68
```

(2) INFORMATION FOR SEQ ID NO: 107:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 107:

```
GGGAGGACGA UGCGGUUAUG GGCGUCAACA CCGCUAUUAC AACUUUCGCC        50

UCCAGACGAC UCGCCCGA                                          68
```

(2) INFORMATION FOR SEQ ID NO: 108:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 108:

```
GGGAGGACGA UGCGGAGCAA GGUUACGCCG UCGGACCCUG CUGCCAACAU        50

CCUCCCCAGA CGACUCGCCC GA                                     72
```

(2) INFORMATION FOR SEQ ID NO: 109:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 109:

```
GGGAGGACGA UGCGGGUCAA GGUUACGCCG UCGGACCCUA CUGCCCCCAG          50

ACGACUCGCC CGA                                                  63
```

(2) INFORMATION FOR SEQ ID NO: 110:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 110:

```
GGGAGGACGA UGCGGCUCCU AUAUUCAUGU UAUUGUUUUU UUCUUCCAGC          50

UUGCCCCAGA CGACUCGCCC GA                                        72
```

(2) INFORMATION FOR SEQ ID NO: 111:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 111:

```
GGGAGGACGA UGCGGAGAUA AUUAUCAGCG GUGGACGGGG UGCCGGUACU          50

GCCGCCAGAC GACUCGCCCG A                                         71
```

(2) INFORMATION FOR SEQ ID NO: 112:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 112:

```
GGGAGGACGA UGCGGUGCCU UUAGCCUAAG UUGAUCUAUU CAGCUUUCUG          50
```

```
CCGCAGACGA CUCGCCCGA                                                  69

(2) INFORMATION FOR SEQ ID NO: 113:

(i) SEQUENCE CHARACTERISTICS:
         (A) LENGTH:  72 base pairs
         (B) TYPE:  nucleic acid
         (C) STRANDEDNESS:  single
         (D) TOPOLOGY:  linear (ii) MOLECULE TYPE:  RNA (ix) FEATURE:
         (D) OTHER INFORMATION:  All pyrimidines are 2'-F modified (xi) SEQUENCE DESCRIPTION:  SEQ ID NO: 113:

GGGAGGACGA UGCGGCCCAA GGUUACGCCG UCGGACCCUA CUGCCAACUU                 50

CCUCCCCAGA CGACUCGCCC GA                                              72

(2) INFORMATION FOR SEQ ID NO: 114:

(i) SEQUENCE CHARACTERISTICS:
         (A) LENGTH:  70 base pairs
         (B) TYPE:  nucleic acid
         (C) STRANDEDNESS:  single
         (D) TOPOLOGY:  linear (ii) MOLECULE TYPE:  RNA (ix) FEATURE:
         (D) OTHER INFORMATION:  All pyrimidines are 2'-F modified (xi) SEQUENCE DESCRIPTION:  SEQ ID NO: 114:

GGGAGGACGA UGCGGUGCCU UUAGCCUGAG UAUACUGAUG UAUAUUCUCU                 50

GCCGCAGACG ACUCGCCCGA                                                 70

(2) INFORMATION FOR SEQ ID NO: 115:

(i) SEQUENCE CHARACTERISTICS:
         (A) LENGTH:  70 base pairs
         (B) TYPE:  nucleic acid
         (C) STRANDEDNESS:  single
         (D) TOPOLOGY:  linear (ii) MOLECULE TYPE:  RNA (ix) FEATURE:
         (D) OTHER INFORMATION:  All pyrimidines are 2'-F modified (xi) SEQUENCE DESCRIPTION:  SEQ ID NO: 115:

GGGAGGACGA UGCGGUAGCG CGAGUUCAAC ACCGCAUGUG ACUCUUUCGC                 50

CUCCCAGACG ACUCGCCCGA                                                 70

(2) INFORMATION FOR SEQ ID NO: 116:

(i) SEQUENCE CHARACTERISTICS:
         (A) LENGTH:  72 base pairs
         (B) TYPE:  nucleic acid
         (C) STRANDEDNESS:  single
         (D) TOPOLOGY:  linear (ii) MOLECULE TYPE:  RNA (ix) FEATURE:
         (D) OTHER INFORMATION:  All pyrimidines are 2'-F modified (xi) SEQUENCE DESCRIPTION:  SEQ ID NO: 116:

GGGAGGACGA UGCGGAUCCU UUUUUUAGCU UUUUUCUUUU UCCUGCCCCA                 50
```

CUUCCCCAGA CGACUCGCCC GA                                                72

(2) INFORMATION FOR SEQ ID NO: 117:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 117:

GGGAGGACGA UGCGGUGCAA GGUUACGCCG UCGGACCCUG CUGCCAACAU                   50

CCUCCCCAGA CGACUCGCCC GA                                                72

(2) INFORMATION FOR SEQ ID NO: 118:

(i) SEQUENCE CHARACTERISTICS:
        (A) LENGTH:  69 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 118:

GGGAGGACGA UGCGGGGGCU UUUCCUUUAG UACUUUUUUG UUUCGCUCCC                   50

CCCCAGACGA CUCGCCCGA                                                    69

(2) INFORMATION FOR SEQ ID NO: 119:

(i) SEQUENCE CHARACTERISTICS:
        (A) LENGTH:  69 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 119:

GGGAGGACGA UGCGGUGCCU UUAGUCUGAA UCUUACCAUG CGAUUUUCUG                   50

CCGCAGACGA CUCGCCCGA                                                    69

(2) INFORMATION FOR SEQ ID NO: 120:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 120:

GGGAGGACGA UGCGGAACAA GGUUACUCCG UCGGACCCUG CUGCCAACAU          50

CCUCCCCAGA CGACUCGCCC GA                                       72

(2) INFORMATION FOR SEQ ID NO: 121:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 121:

GGGAGGACGA UGCGGGACUC UUGUCUGCGA UUCAACUCGU AGGUCUUCUC          50

ACGUGCAGAC GACUCGCCCG A                                        71

(2) INFORMATION FOR SEQ ID NO: 122:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 122:

GGGAGGACGA UGCGGUUAGG GGCGUCAACA CCGCUAUCAU AACUUUCGCU          50

UCCCCAGACG ACUCGCCCGA                                          70

(2) INFORMATION FOR SEQ ID NO: 123:

(i) SEQUENCE CHARACTERISTICS:
        (A) LENGTH:  69 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 123:

GGGAGGACGA UGCGGUUAGG GGCGUCAACA CCGCUAUUCA ACCUUCGCUU          50

CCCCAGACGA CUCGCCCGA                                           69

(2) INFORMATION FOR SEQ ID NO: 124:

(i) SEQUENCE CHARACTERISTICS:
        (A) LENGTH:  69 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 124:

```
GGGAGGACGA UGCGGUUAGG GCGUCAACAC CGCUAUUACA ACUUUCGCCU      50

CCCCAGACGAC UCGCCCGA                                        69

(2) INFORMATION FOR SEQ ID NO: 125:

(i) SEQUENCE CHARACTERISTICS:
        (A) LENGTH:  51 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 125:

GGGAGGACGA UGCGGGGUGU CGUCUUUCAA CCCCUCAGAC GACUCGCCCG       50

A                                                            51

(2) INFORMATION FOR SEQ ID NO: 126:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 126:

GGGAGGACGA UGCGGUUAUG GGCGUCAACA CCGCUAUUAC AACUUUCGCC       50

UCCCCAGACG ACUCGCCCGA                                        70

(2) INFORMATION FOR SEQ ID NO: 127:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION:  SEQ ID NO: 127:

GGGAGGACGA UGCGGCCCAA GGUUACGCCG UCGGACCCUG CUGCAAACAU       50

CCUCCCCAGA CGACUCGCCC GA                                     72

(2) INFORMATION FOR SEQ ID NO: 128:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified
```

(xi) SEQUENCE DESCRIPTION: SEQ ID NO: 128:

GGGAGGACGA UGCGGUUAUG GGCGUCAACA CCGCUAUUAC AGUUUCGCC      50

UCCCCCAGAC GACUCGCCCG A      71

(2) INFORMATION FOR SEQ ID NO: 129:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION: SEQ ID NO: 129:

GGGAGGACGA UGCGGUUAGG GGCGUCAACA CCGCUAUUAC AAUCUUCGCU      50

UUCCCAGACG ACUCGCCCGA      70

(2) INFORMATION FOR SEQ ID NO: 130:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION: SEQ ID NO: 130:

GGGAGGACGA UGCGGGCCAA GGUUACGCCG UCGGACCCUG CUGCCAACAU      50

CUUCCCCAGA CGACUCGCCC GA      72

(2) INFORMATION FOR SEQ ID NO: 131:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION: SEQ ID NO: 131:

GGGAGGACGA UGCGGUUAGG GGCGUCAACA CCGCUAUUAC AAUCUUCGUC      50

UUCCCAGACG ACUCGCCCGA      70

(2) INFORMATION FOR SEQ ID NO: 132:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  RNA (ix) FEATURE:
        (D) OTHER INFORMATION:  All pyrimidines are 2'-F modified (xi) SEQUENCE DESCRIPTION: SEQ ID NO: 132:

GGGAGGACGA UGCGGGUCAA GUUUACGCCG UCGGACCCUG CUGCCAACAU          50

CCUCCCCAGA CGACUCGCCC GA          72

(2) INFORMATION FOR SEQ ID NO: 133:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 133:

GGGAGGACGA UGCGGUUCAA GGUUACGCCG UCGGACCCUG CUGCCAACAU          50

CCUCCCCAGA CGACUCGCCC GA          72

(2) INFORMATION FOR SEQ ID NO: 134:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 134:

GGGAGGACGA UGCGGCUCAA GGUUACGCCG UCGGACCCUG CUGCCAACAU          50

CCUCCCCAGA CGACUCGCCC GA          72

(2) INFORMATION FOR SEQ ID NO: 135:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 135:

GGGAGGACGA UGCGGUUAGG GGCUUCAACA CCGCUAUUAC AUUCUUCGCC          50

UCCCCAGACG ACUCGCCCGA          70

(2) INFORMATION FOR SEQ ID NO: 136:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:

(D) OTHER INFORMATION: All pyrimidines are 2'-F modified (xi) SEQUENCE DESCRIPTION: SEQ ID NO: 136:

GGGAGGACGA UGCGGCACAA AGUUACGCCG UAGGACCCUG CUGCCAACAU           50

CCUCCCCAGA CGACUCGCCC GA                                        72

(2) INFORMATION FOR SEQ ID NO: 137:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 137:

GGGAGGACGA UGCGGGGAUG GUCAGUUUCG GUUUUUCAUA UGUUUAUUUU           50

CCCCCCCAGA CGACUCGCCC GA                                        72

(2) INFORMATION FOR SEQ ID NO: 138:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 138:

GGGAGGACGA UGCGGUAUUG ACUUUUGUUU CUUUUUCUUU GCCUGGUCCC           50

CAGACGACUC GCCCGA                                               66

(2) INFORMATION FOR SEQ ID NO: 139:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 139:

GGGAGGACGA UGCGGUUAGG GGCGUCAACA CCGCUAUUAC AACUUUCGCU           50

UCCCCAGACG ACUCGCCCGA                                           70

(2) INFORMATION FOR SEQ ID NO: 140:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA -continued (ix) FEATURE:
    (D) OTHER INFORMATION: All pyrimidines are 2'-F modified (xi) SEQUENCE DESCRIPTION: SEQ ID NO: 140:

GGGAGGACGA UGCGGCUUCU UUUUCUUCUU UUCUUUAUGU CUUCUUCAUG        50

CCGCAGACGA CUCGCCCGA                                          69

(2) INFORMATION FOR SEQ ID NO: 141:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 141:

GGGAGGACGA UGCGGGACCN UUGUNUGCGA UUCAACUCGU AGGUCUUCUC        50

ACGUGCAGAC GACUCGCCCG A                                      71

(2) INFORMATION FOR SEQ ID NO: 142:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 142:

GGGAGGACGA UGCGGUUAUG GGCGUCAACA CCGCUAUUAC AACUUUCGCC        50

CCCCAGACGA CUCGCCCGA                                          69

(2) INFORMATION FOR SEQ ID NO: 143:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-F modified (xi) SEQUENCE DESCRIPTION: SEQ ID NO: 143:

GGGAGGACGA UGCGGUUAUG GGUGUCAACA CCGCUAUUAC AACUUUCGCC        50

UCCCCAGACG ACUCGCCCGA                                         70